United States Patent [19]

Lambeir et al.

[11] Patent Number: 5,310,665
[45] Date of Patent: May 10, 1994

[54] GLUCOSE ISOMERASES HAVING ALTERED SUBSTRATE SPECIFICITY

[75] Inventors: Anne-Marie Lambeir, Heverlee; Ignace Lasters, Antwerpen, both of Belgium; Wilhemus J. Quax, Voorschoten; Jan M. Van der Laan, Groningen, both of Netherlands

[73] Assignee: Gist-brocades, N.V., Delft, Netherlands

[21] Appl. No.: 637,870

[22] Filed: Jan. 4, 1991

[30] Foreign Application Priority Data

Jan. 4, 1990 [EP] European Pat. Off. ......... 90200029.8

[51] Int. Cl.⁵ .................. C12P 19/24; C12N 9/92
[52] U.S. Cl. ............................. 435/94; 435/234
[58] Field of Search ................. 435/234, 233, 94

[56] References Cited

U.S. PATENT DOCUMENTS 4,894,331 1/1990 Ratzkin ........................... 435/94
5,041,378 8/1991 Drummond et al. ............. 435/234

FOREIGN PATENT DOCUMENTS 0351029  1/1990  European Pat. Off. .
WO88/08028 10/1988 PCT Int'l Appl. .
WO89/01520  2/1989 PCT Int'l Appl. .
WO90/00196  1/1990 PCT Int'l Appl. .

OTHER PUBLICATIONS

Chen, *Process Biochemistry* (Jun./Jul. 1980) pp. 30–35.
Chen, *Process Biochemistry* (Aug./Sep. 1980) pp. 36–41.
Jeffries, *Trends in Biotechnol.* (1985) 3:208–212.
Wells et al., *Proc. Natl. Acad. Sci.* (1987) 84:5167–5171.
Wilks et al., *Science* (1988) 242:1541–1544.
Lindberg et al., *Nature* (1989) 339:632–634.
Amore et al., *Nucl. Acids. Res.* (1989) 17(18):7515.

*Primary Examiner*—Charles L. Patterson, Jr.
*Attorney, Agent, or Firm*—Morrison & Foerster

[57] ABSTRACT

A method for selecting amino acid residues is disclosed which upon replacement will give rise to an enzyme with an altered substrate specificity. New mutant glucose isomerases with an altered substrate specificity are provided according to this method. These altered properties are useful in starch degradation and in other sugar conversion reactions.

16 Claims, 4 Drawing Sheets

\* CONSERVED RESIDUE  —— H-BOND DISTANCE  ---- DISTANCE WITH METALS

```
Aml   1                                                         MSVQATRED KF SFG LMTVGWQ AR.DAFGDATR
Amp   1                                                         MSLQATPDD KF SFG LMTVGWQ AR.DAFGDATR
Sv1   1                                                         MNYQPTPED RF TFG LMTVGWQ GR.DPFGDATR
Smu   1                                                         MSFQPTPED RF TFG LMTVGWQ GR.DPFGDATR
Sth   1                                                         MSYQPTPED RF SFG LMTVGWQ GR.DPFGDATR
Art   1                                                         MSVQPTPAD HF TFG LMTVGWT GA.DPFGVATR
Bsu   1    MAQSHSSSVNYFGSVNKVVFEGKASTNPLAFKYYNPQEVIGGKTMKEHLRFSIAYWH TFTADGTD VF GAA TMQRPWD HY.KGM.DLAR
Eco   1        MQAYFDQLDRVRYEGSKSSNPLAFRHYNPDELVLGKRMEEHLRFAACYWH TFCWNGAD MF GVG AFNRPWQ QPGEAL.ALAK
Lxy   1          MAYFNDIAPIKYEGTKTKNMFAFRHYNPEEVVAGKTMEEQLHFALAFWH TITMDGSD PF GGA TMERPWD LEGGSELDRAH

Aml  31 TAL DPV.EAVH KLAEIG A YGI T FHDDDLVPF GS D....AQTRDGI IAGFKKALDE TG LIV PMVTT NLFTHPVFKD GGFTSN DRSV
Amp  31 PVL DPI.EAVH KLAEIG A YGV T FHDDDLVPF GA D....AATRDGI VAGFSKALDE TG LIV PMVTT NLFTHPVFKD GGFTSW DRSV
Sv1  31 QAL DPA.ESVR RLSELG A YGV T FHDDDLIPF GS S....DTERESH IKRFRQALDA TG MKV PMATT NLFTHPVFKD GAFTAN DRDV
Smu  31 PAL DPV.ETVQ RLAELG A YGV T FHDDDLIPF GS S....DTERESH IKRFRQALDA TG MTV PMATT NLFTHPVFKD GGFTAN DRDV
Sth  31 RPL DPV.GTVQ RLAELG A YGV T FHDDDLIPF GA S....EAEREAH VKRFRQALDA TG MTV PMATT NLFTHPVFKD GAFTAN DRDV
Art  31 KNL DPV.EAVH KLAEIG A YGI T FHDNDLIPF DA T....EAEREKI LGDFNQALKD TG LKV PMVTT NLFSHPVFKD GGFTSN DRSI
Bsu  88 ARV EAAFEMFE KL...D A PFF A FHDRDIAPE GS TLKETNQNLDII VGMIKDYMRD SN VKL LWNTA NMFTNPRFVH GAATSC NADV
Eco  80 RKA DVAFEFFH KL...H V PFY C FHDVDVSPE GA SLKEYINNFAQM VDVLAGKQEE SG VKL LWGTA NCFTNPRYGA GAATNP DPEV
Lxy  80 RRV DAFFEIAE KL...G V KYY C FHDIDIAPT GN SLKEFYANLDEI TDHLLEKQKA TG IKL LWNTA NMFSNPRYMN GVSTSN RAEV

Aml 111 RRYAIRKVLR QMDLGAELG A KTLVLW GGRE GAEYDSAK DV SAALDRYREA LNLLAQYSED RG YGL RFAIE PKPNEPRGDI
Amp 111 RRYAIRKVLR QMDLGAELG A KTLVLW GGRE GAEYDSAK DV GAALDRYREA LNLLAQYSED QG YGL RFAIE PKPNEPRGDI
Sv1 111 RRYALRKTIR NIDLAVELG A SVYVAW GGRE GAESGAAK DV RDALDRMKEA FDLLGEYVTE QG YDL KFAIE PKPNEPRGDI
Smu 111 RRYALRKTIR NIDLAAELG A KTYVAW GGRE GAESGGAK DV RDALDRMKEA FDLLGEYVTA QG YDL HFAIE PKPNEPRGDI
Sth 111 RRYALRKTIR NIDLAVELG A RTYVAW GGRE GAESGAAK DV RAALDRMKEA FDLLGEYVTS QG YDI RFAIE PKPNEPRGDI
Art 111 RRFALAKVLH NIDLAAEMG A ETFVMW GGRE GSEYDGSK DL AAALDRMREG VDTAAGYIKD KG YNL RIALE PKPNEPRGDI
Bsu 168 FAYAAAQVKK GLETAKELG A ENYVFW GGRE GYETLLNT DL KFELDNLARF MHMAVDYAKE IE YTG QFLIE PKPKEPTTHQ
Eco 162 FSWAATQVVT AMEATHKLG V AMEATHKLG GGRE GYETLLNT DL RQEREQLGRF MQMVVEHKHK IG FQG TLLIE PKPQEPTKHQ
Lxy 162 FAYGAAQVKK GLELSKKLG G ENYVFW GGRE GYESLLNT DM GLEMDHMAKF FHLAIDYAKS IN HLP IFLIE PKPKEPMTHQ
```

FIG. 2A

```
Am1 191 LLP TAGHAIA FVQ ELERPE L FGINPET GHE QMSNL NFTQG IAQALWHK K L FHIDL NGQHG .PKFDQDLVFG HG DLLNAFSL
Amp 191 LLP TAGHAIA FVQ ELERPE L FGINPET GHE QMSNL NFTQG IAQALWHK K L FHIDL NGQHG .PKFDQDLVFG HG DLLNAFSL
Sv1 191 LLP TVGHALA FIE RLERPE L YGVNPEV GHE QMAGL NFPHG IAQALWAG K L FHIDL NGQSG .IKYDQDLRFG AG DLRAAFWL
Smu 191 LLP TVGHALA FIE RLERPE L YGVNPEV GHE QMAGL NFPHG IAQALWAG K L FHIDL NGQSG .IKYDQDLRFG AG DLRAAFWL
Sth 191 LLP TVGHALA FIE RLERPE L FGVNPEV GHE QMAGL NFPHG IAQALWAG K L FHIDL NGQRG .IKYDQDLRFG AG DLRAAFWL
Art 191 FLP TVGHGLA FIE QLEHGD I VGLNPET GHE QMAGL NFTHG IAQALWAE K L FHIDL NGQRG .IKYDQDLVFG HG DLTSAFFT
Bsu 248 YDT DAATTIA FLK QYGLDN H FKLNLEA NHA TLAGH TFEHE LRMARVHG L L GSVDA NQGHP LLGWDTDE.FP TD LYSTTLAM
Eco 242 YDY DAATVYG FLK QFGLEK E IKLNIEA NHA TLAGH SFHHE IATAIALG L F GSVDA NRGDA QLGWDTDQ.FP NS VEENALVM
Lxy 242 YDF DSATALA FLQ KYDLDK Y FKLNLET NHA WLAGH TFEHE LNTARTFN A L GSJDA NGGNY LLGWDTDE.FP TL VIDITLAM

Am1 271 VDLLE NG.PDG APAYDGP RHF D YKPSRT..E DY DGVWESAKAN IRMYLLLKER AKAFRA DPEV QEALAASKVA ELKTPILNPG
Amp 271 VDLLE NG.PDG GPAYDGP RHF D YKPSRT..E DF DGVWESAKDN IRMYLLLKER AKAFRA DPEV QAALAESKVD ELRTPTLNPG
Sv1 271 VDLLE RA...G ...YAGP RHF D FKPPRT..E DF DGVWASAAGC MRNYLILKDR AAAFRA DPQV QEALAAARLD ELARPT..AE
Smu 271 VDLLE TA...G ...YEGP RHF D FKPPRT..E DF DGVWASAAGC MRNYLILKDR AAAFRA DPEV QEALRAARLD QLAQPT..AA
Sth 271 VDLLE SS...G ...YDGP RHF D FKPPRT..E DL DGVWASAAGC MRNYLILKDR SAAFRA DPEV QEALRASRLD QLAQPT..AA
Art 271 VDLLE NGFPNG GPKYTGP RHF D YKPSRT..D GY DGVWDSAKAN MSMYLLLKER ALAFRA DPEV QEAMKTSGVF ELGETTLNAG
Bsu 328 YEILQ NGGL.G ....SGG LNF D AKVRRSSFE PD DLVYAHIAGM DAFARGLKVA HKLI.E DRVF EDVIQHRYRS F.TEGIGLEI
Eco 322 YEILK AGGF.T ....TGG LNF D AKVRRQSTD KY DLFYGHIGAM DTMALALKIA ARMI.E DGEL DKRIAQRYSG W.NSELGQQI
Lxy 322 HQILL NGGL.G ....KGG INF D AKVRRTSFK AE DLILAHIAGM DTYARALKGA AAII.E DKFL SDIVDERYSS YRNTEVGQSI

Am1 351 EGYAELLADR SAFED.Y..DAD AVGAKGFGFVK .LNQLAIEHLL GAR
Amp 351 ETYADLLADR SAFED.Y..DAD AVGAKGYGFVK .LNQLAIDHLL GAR
Sv1 344 DGLAALLADR SAYDT.F..DVD AAAARGMAFEH .LDQLAMDHLL GAR
Smu 344 DGLDALLADR AAFED.F..DVD AAAARGMAFEH .LDQLAMDHLL GARG
Sth 348 DGLQ
Art 352 ESAADLMNDS ASFAG.G..DAE AAAERNFAFIR .LNQLAIEHLL GSR
Bsu 404 TEGRANFHTL EQYALNNK.TIK NESGRQERLKP ILNQ
Eco 380 LKGQMSLADL AKYAQEHHLSPV HQSGRQEQLEN LVNHYLFDK
Lxy 380 ENGTATFESL AAFALEYGDDIE LDSNHLEYIKS VLNDYLV
```

FIG. 2B

GLUCOSE ISOMERASES HAVING ALTERED SUBSTRATE SPECIFICITY

TECHNICAL FIELD

The present invention relates to the application of protein engineering technology to improve the properties of enzymes. Specifically, the present invention discloses a method for selecting amino acids which upon substitution give rise to an altered substrate specificity. The method is applied to glucose isomerases. In other aspect the invention provides glucose isomerases with an altered substrate specificity. These new glucose isomerases can advantageously be used in industrial processes, for example in the production of high fructose corn syrups (HFCS).

BACKGROUND OF THE INVENTION

Glucose isomerases catalyze the reversible isomerization of glucose to fructose. Fructose is nowadays commonly applied as sugar substitute due to its higher sweetness compared to e.g. sucrose and glucose.

Many microorganisms are known to produce glucose isomerase, see for example the review articles by Wen-Pin Chen in Process Biochemistry, 15 June/July (1980) 30–41 and August/September (1980) 36–41, in which a large number of microorganisms, capable of producing glucose isomerase, are listed.

Several microorganisms can be used for the industrial production of glucose isomerases, among these *Streptomyces Ampullariella* and Actinoplanes are well known. The Wen-Pin Chen reference describes culture conditions for the microorganisms and recovery and purification methods for the produced glucose isomerases.

Generally the naturally occurring glucose isomerases also show a high affinity for sugars other than glucose. In this respect D-xylose, D-ribose, L-arabinose, D-allose and 6-deoxyglucose were found to be substrates of this enzyme. The $K_m$ values of D-glucose, D-xylose and D-ribose, were shown to vary from microorganism to microorganism and were reported to be in the range of 0.086–0.920, 0.005–0.093 and 0.35–0.65M, respectively.

The $K_m$ values for xylose are significantly lower than for glucose, which implies that the correct name for the enzyme is in fact xylose isomerase. Furthermore, the $V_{max}$ of the commonly used glucose isomerases is higher on xylose than on glucose, which also suggest that xylose isomerase is a better name.

Since glucose isomerase is active on different substrates it may be advantageous to alter the substrate specificity depending on the desired reaction product, the specific process in which it is used or the wish to avoid unwanted side-products.

For the application of glucose isomerase in HFCS production a higher $V_{max}$ and a lower $K_m$ on glucose would be useful properties, since the reaction time and the enzyme costs would be reduced.

Another application of glucose isomerase is in the conversion of xylose to ethanol (Jeffries, T. W., Trends Biotechnol. 3 (1985) 208). A higher activity ($V_{max}$) on xylose and/or a better affinity for xylose would be useful properties for this application.

The digestibility and the taste of feed for monogastric animals can be improved if glucose is converted enzymatically into fructose. In practice the application of glucose isomerase is hampered by the xylose isomerisation activity, which causes an unwanted formation of xylulose in feed. A glucose isomerase with no or reduced specificity ($V_{max}$ or $K_m$) for xylose would be preferred for application in feed pretreatment.

Clearly, there is a need for altering the substrate specificity of glucose isomerases which would at the same time widen the field of the application of this enzyme.

Recently redesigning of the specific activity of enzymes with the aid of protein engineering techniques has been described. Wells et al. (Proc. Natl. Acad. Sci. U.S.A. 84 (1987) 5167) show an example for subtilisin. *Bacillus licheniformis* and *B. amyloliquefaciens* serine proteases differ by 31% (86 amino acid residues) in protein sequence and by a factor of 60 in catalytic efficiency on certain substrates. By substituting 3 of the 86 different amino acids from the *B. amyloliquefaciens* sequence by the corresponding *B. licheniformis* residues the catalytic activity of the mutant enzyme was improved nearly 60 fold.

In another paper it is described how a lactate dehydrogenase was changed into a malate dehydrogenase by mutating glutamine 102 into arginine 102 (Wilks et al., Science 242 (1988) 1541).

In both cases referred to above, serine protease and lactate dehydrogenase, the modification proposal was based on the comparison of the molecule to be modified and naturally occurring enzymes, which already showed the desired substrate specificity. In the same way the specificity of cytochrome $p450_{15\alpha}$ was changed into the specificity of cytochrome $p450_{coh}$ by replacing Leu209 with Phe209 (Lindberg and Negishi, Nature 339 (1989) 632).

For glucose isomerase no naturally occurring enzyme is known, which shows a better specificity for glucose than for xylose. The above-mentioned method, based on the comparison of active sites of homologous enzymes having a different substrate specificity, can therefore not be applied to glucose isomerase.

WO 89/01520 (Cetus) lists a number of muteins of the xylose isomerase which may be obtained from *Streptomyces rubiginosus* and that may have an increased stability. The selection of possible sites that may be mutated is based on criteria differing from the ones used in the present invention. More than 300 mutants are listed but no data are presented concerning the characteristics and the alterations therein of the mutant enzyme molecules.

SUMMARY OF THE INVENTION

The present invention discloses a method for selecting amino acids which upon replacement lead to an altered substrate specificity of a given enzyme. This method, which is generally applicable, is used to alter the substrate specificity of glucose isomerase.

Thus, the invention also provides glucose isomerases with altered substrate specificities. This altered substrate specificity is expressed in terms of an altered substrate binding capacity and/or an altered catalytic activity Specifically, mutant glucose isomerases are provided with both an absolute and a relative change in substrate binding capacity and catalytic activity on glucose and xylose as substrates.

Furthermore, mutant glucose isomerases are provided which show that parameters, such as, increased stability (expressed in terms of decay constant) and altered substrate specificity can be combined into a single molecule by adding the respective mutations that have these effects.

The mutant glucose isomerases are obtained by the expression of a gene encoding said glucose isomerase enzyme having an amino acid sequence which differs at least in one amino acid from the wildtype glucose isomerase enzyme.

BRIEF DESCRIPTION OF THE FIGURES

FIGS. 2A and 2B show the alignment of the amino acid sequences of glucose isomerases obtained from different microorganisms. The complete sequence of *Actinoplanes missouriensis* glucose isomerase is given. The amino acid sequence of Ampullariella glucose isomerase differs from that of the published sequences (Saari, J. Bacteriol., 169, (1987) 612) by one residue: Proline 177 in the published sequence was found to be Arginine.

The *Streptomyces thermovulgaris* sequence has only been established up to amino acid 351. Undetermined residues are left blank. A dot indicates the absence of an amino acid residue at this position as compared to any of the other sequences. The different species are indicated by the following symbols:

| | |
|---|---|
| Ami. | *Actinoplanes missouriensis* DSM 4643 (SEQ. ID. NO: 1) |
| Amp. | *Ampullariella species* ATCC 31351 (SEQ. ID. NO: 2) |
| Svi. | *Streptomyces violaceoruber* LMG 7183 (SEQ. ID. NO: 3) |
| Smu. | *Streptomyces murinus* (SEQ. ID. NO: 4) |
| Sth. | *Streptomyces thermovulgaris* DSM 40444 (SEQ. ID. NO: 5) |
| Art. | *Arthrobacter species* (SEQ. ID. NO: 6) |
| Bsu. | *Bacillus subtilis* (SEQ. ID. NO: 7) |
| Eco. | *Escherichia coli* (SEQ. ID. NO: 8) |
| Lxy. | *Lactobacillus xylosus* (SEQ. ID. NO: 9) |

The secondary structure assignment was made in the structure of *Actinoplanes missouriensis*. Helices in the barrel are enclosed by solid lines. Shaded boxes indicate β-strands.

Figure 3:
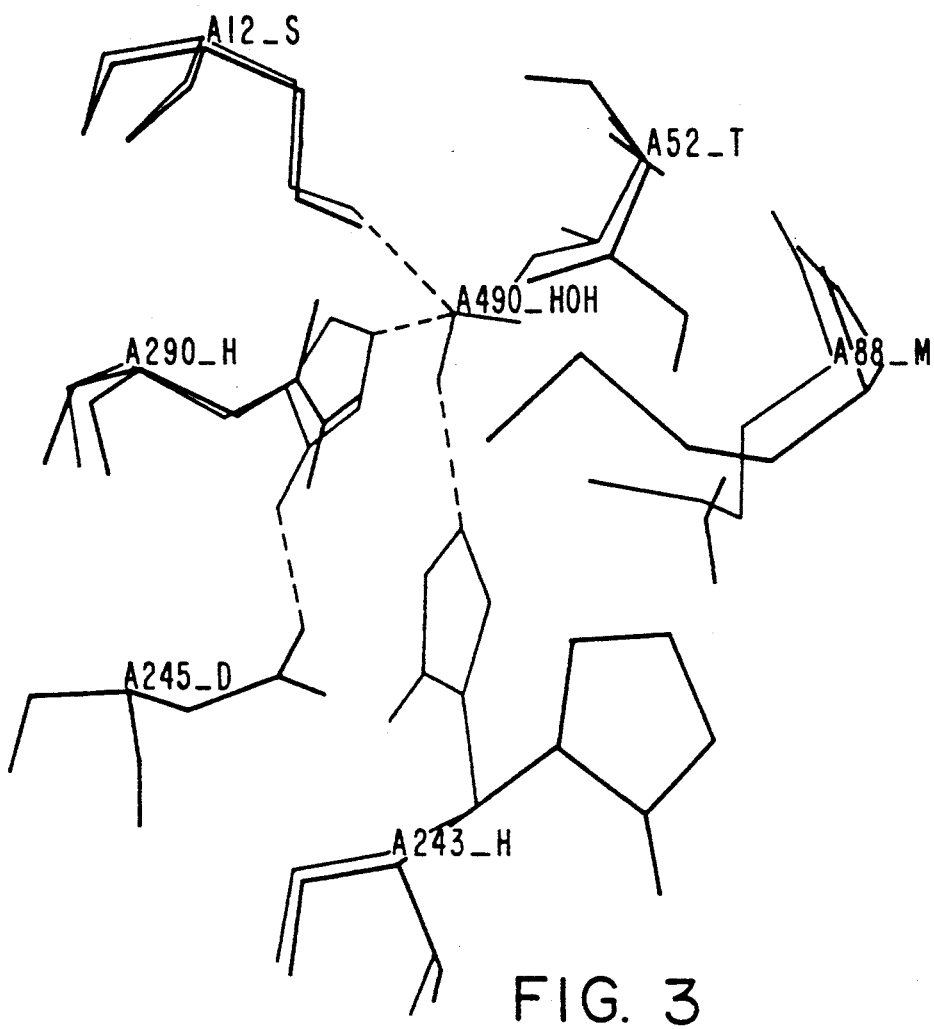

FIG. 3 shows a comparison of the H290N mutant (bold) with the wildtype-sorbitol-Mg structure

DETAILED DESCRIPTION OF THE INVENTION

The present invention discloses a method for selecting amino acids, in an enzyme, that upon substitution give rise to an altered substrate specificity. To obtain such a mutant enzyme the DNA sequence encoding this enzyme is altered in such a way that the encoded enzyme has one or more selected amino acid replacements. The altered DNA is expressed in a desired host/vector system. To select appropriate (point) mutations a rational approach is taken, relying on the well coordinated application of protein crystallography; molecular modelling and computational methods, enzymology and kinetics, molecular biology and protein chemistry techniques. The strategies for the identification of target amino acid sites are innovative in a sense that it is recognized that point mutations rarely cause local perturbations, but affect several different properties of the protein structure at once, causing a change in different properties as well. Therefore, although the described strategies make use of well established structure-function relationships, they also provide a rational way to avoid or correct unwanted alterations of kinetic and structural properties.

Alteration of Substrate Specificity by Replacement of Appropriate Amino Acids To modulate the substrate binding to the active site of an enzyme, the following general rules can be applied in sequential order, provided that data are available concerning the Three-Dimensional (3D) structure for the enzyme-substrate or enzyme-substrate-analogue/inhibitor complexes:

a) select all residues and crystallographically assigned water molecules which have at least one atom within a sphere of 4Å surrounding the atoms of the substrate or of a substrate analogue/inhibitor bond in the active site;

b) select all the residues which are in Van der Waals contact with the residues and water molecules obtained by application of criterion a);

c) discard from the recorded list of residues and water molecules those that are implied in catalysis, cofactor binding (such as metal ions and nucleotides) and essential intersubunit interactions (in the case of oligomeric enzymes);

d) discard those residues and water molecules that interfere with the structural role of the above-selected residues. Model building and analysis of the conserved nature of the target residues can be used to identify an essential structural role;

e) to modulate the substrate affinity, one or more of the above-selected residues can be substituted by alteration of the genetic code to change one or more of the following interactions and properties:

e1) steric hindrance through altering the residue size;
  e2) hydrophobicity/polarity of the substrate surroundings;
  e3) solvation of the substrate surroundings either by providing side chains that solvate via hydrogen bonding to groups within the substrate or through substitutions that alter the water distribution within the surroundings of the substrate;
  e4) flexibility of individual residues, segments or the overall protein structure by substitutions that disrupt hydrogen bonding networks, decrease the local packing density in the surroundings of the substrate or introduce cavities.

The above set of rules is a general one which can in principle be applied to all enzymes provided that enough structural data are available. In order to demonstrate the feasibility of this set of rules a specific example will be discussed below.

Application of the General Rules to Modulate the Substrate Specificity of Glucose Isomerase Although the selection of residues by applying criteria a) through e) as given above will be demonstrated here using the specific example of *Actinoplanes missouriensis* glucose isomerase, it is clear that due to extensive homology similar substitution sites can be selected in glucose isomerases obtained from other species. The mentioned sequence homology is demonstrated in FIG. 2 which gives an alignment of glucose isomerases obtained from; *Actinoplanes missouriensis*, *Ampullariella* species, *Streptomyces violaceoruber*, *Streptomyces murinus*, *Streptomyces thermovulgaris*, *Arthrobacter* species, *Bacillus subtilis*, *Escherichia coli* and *Lactobacillus xylosus*. The approach described above would also give rise, after amino acid replacement at corresponding positions in the glucose isomerases from the other species, to an altered substrate specificity of other glucose isomerases.

In general, it can be assumed that where the overall homology is greater than 65%, preferably greater than 74% (minimal homology between *Actinoplanes missouriensis* and Streptomyces glucose isomerase, according to Amore and Hollenberg, Nucl. Acids Res. 17, 7515 (1989)), and more preferably greater than 85% and where the 3D structure is similar, amino acid replacements will lead to similar changes in substrate specificity. With similar changes in substrate specificity we mean the direction in which the kinetic parameters change and not the magnitude. Specifically one expects the glucose isomerases from species belonging to the order of the Actinomycetales to have such a high degree of similarity that the alteration of substrate specificities due to amino acid replacements at the selected sites are similar. *Actinoplanes missouriensis* is the preferred source of glucose isomerase to mutate.

Changes in substrate specificity according to the present invention include all combinations of increase and decrease of $V_{max}$ and $K_m$ for both glucose and xylose. A person skilled in the art will understand that this encompasses the changes in other kinetic parameters. Furthermore, the specificities for other substrates will inherently be changed also. The proposed rules for changing the substrate specificity are not restricted to the mentioned substrates, they can be applied to other substrates. Among these are, D-ribose, L-arabinose, D-allose and 6-deoxyglucose.

Thus apart from providing a general method for altering the substrate specificity the present invention applies this method to glucose isomerase.

The selected amino acid replacements can be engineered in the DNA encoding the glucose isomerase by methods well known to a person skilled in the art (e.g. site-directed mutagenesis). The DNA encoding the glucose isomerase or its mutants may be cloned on an expression vector and this construct may be transformed to a host wherein the gene is expressed, the mRNA translated and preferably the mature protein, or a precursor, secreted from the cell. Subsequently the protein can be purified. Standard procedures can be found in Maniatis et al. (Cold Spring Harbor, 1st and 2nd edition, 1982 and 1989 respectively).

The application of these methods gives rise to mutant glucose isomerase enzymes, obtained by the expression of a gene encoding said glucose isomerase enzyme having an amino acid sequence which differs at least in one amino acid from the wildtype glucose isomerase enzyme, which mutant glucose isomerase enzyme is characterized in that it exhibits an altered substrate specificity. Instead of single mutants also double mutants may be obtained. Some of these double mutants, aimed at combining the desired properties, show that the properties are at least partially cumulative. Examples are provided, in the present application, of mutants with both an increased specificity for glucose and an increased stability.

The substrate specificity of the new enzymes can be tested on the substrate that is necessary for the desired application. Here special attention is paid to the kinetic parameters concerning glucose and xylose as a substrate and also to the relative changes in these parameters.

Figure 1:
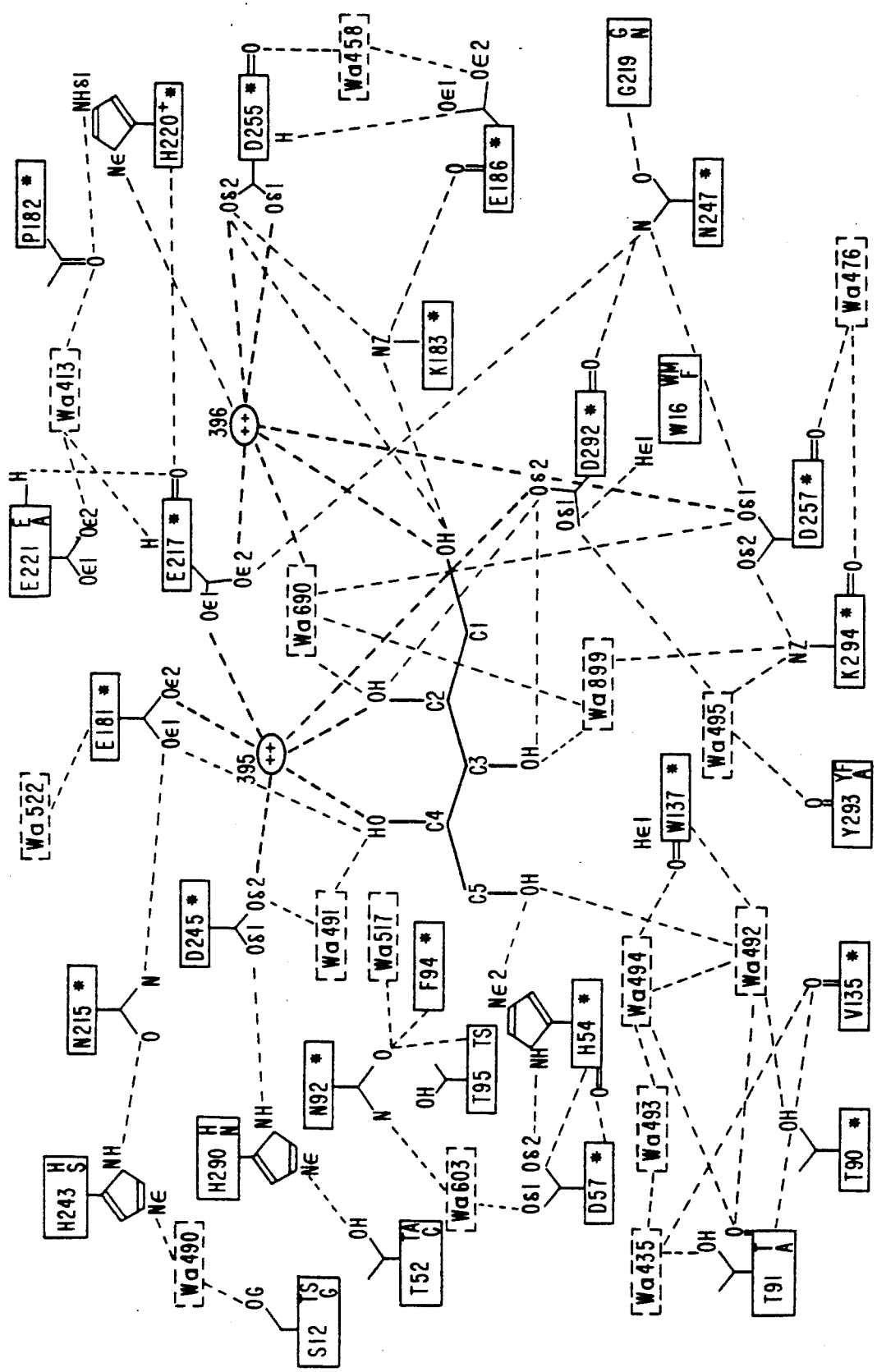
FIG. 1 shows a schematic representation of the active site of glucose isomerase from *Actinoplanes missouriensis*, derived from the three dimensional structure of the glucose isomerase - xylitol complex. The inhibitor is shown in full detail in the centre of the figure. For the amino acid residues only those atoms are drawn which are involved in hydrogen bonding. Residue names are in boxes drawn with solid lines, solvent molecules in boxes drawn with dashed lines. Metal binding sites are represented by ovals numbered 395 and 580. Dashed lines indicate electrostatic interactions: the thin dotted lines represent hydrogen bonds, the fat dashed lines the proposed ligation of the metals. Strictly conserved residues are marked by an asterix. For non-conserved residues the substitutions found in nature are indicated.

FIG. 1 shows a schematic map of residues around the active site of *A. missouriensis*. In the following methods are described to design mutants which have a higher relative specificity for glucose compared to the wildtype enzyme.

Applying the rules given above to glucose isomerase from *Actinoplanes missouriensis* and using the coordinates of the sorbitol-GI-$Co^{2+}$ structure we obtain the following list of residues:

Residues and waters selected by criterion (a): 16Trp, 54His, 88Met, 90Thr, 94Phe, 135Val, 137Trp, 181Glu, 183Lys, 217Glu, 220His, 245Asp, 255Asp, 292Asp, 294Lys, 26Phe and 4 water molecules that are arbitrarily denoted as 491, 492, 690 and 887.

Additional residues were selected by criterion (b). In this case all residues within a sphere of 2Å around the above mentioned residues (criterion (a)) were taken. Giving the following amino acids:

15Leu, 17Thr, 20Trp, 25Ala, 27Gly, 52Thr, 53Phe, 55Asp, 57Asp, 87Pro, 89Val, 91Thr, 92Asn, 93Leu, 95Thr, 133Thr, 134Leu, 136Leu, 138Gly, 140Arg, 179Ala, 180Ile, 182Pro, 184Pro, 186Glu, 215Asn, 216Pro, 218Thr, 219Gly, 221Glu, 243His, 244Ile, 246Leu, 254Phe, 256Gln, 257Asp, 290His, 291Phe, 293Tyr and 295Pro.

The catalytic residues: 54His, 183Lys, 220His; the cation ligands: 181Glu, 217Glu, 221Glu, 245Asp, 255Asp, 292Asp, water 690 and the interface residue: 26Phe; are discarded by applying criterion (c).

Residues 16Trp, 94Phe and 137Trp form a conserved hydrophobic cluster determining the overall shape of the substrate binding pocket and they are therefore discarded by applying criterion (d). Furthermore residue 184Pro is discarded by criterion (d).

The preferred residues to be substituted resulting after application of the above mentioned criteria are shown in Table 1.

TABLE 1

| | | | | |
|---|---|---|---|---|
| 15Leu | 17Thr | 20Trp | 25Ala | 27Gly |
| 52Thr | 53Phe | 55Asp | 57Asp | 87Pro |
| 88Met | 89Val | 90Thr | 91Thr | 92Asn |
| 93Leu | 95Thr | 133Thr | 134Leu | 135Val |
| 136Leu | 138Gly | 140Arg | 179Ala | 180Ile |
| 182Pro | 186Glu | 215Asn | 216Pro | 218Thr |
| 219Gly | 243His | 244Ile | 246Leu | 254Phe |
| 256Gln | 257Asp | 290His | 291Phe | 293Tyr |
| 294Lys | 295Pro | | | |

Single substitutions at these sites and/or combinations of substitutions at the different sites may lead to an improved activity either through relief of steric hindrance or by the modulation of polarity of the sugar environment. Different properties such as modulating the affinity and/or catalytic efficiency for various substrates may be altered in this way.

In the specific case of increasing the specificity for glucose relative to xylose it is important to note that the substrate specificity for wildtype glucose isomerase decreases going from xylose to 6-deoxy-glucose to glucose. The inhibition constant for sorbitol is larger than for xylitol. This observation suggests that steric hindrance upon binding of the larger substrate or inhibitor contributes to the lower specificity. In the crystal structure of the enzyme-sorbitol-cobalt complex from A. missouriensis the following residues are found within 4Å of the hydroxyl group attached to the C6 of the sorbitol: 16Trp, 88Met, 135Val, 90Thr and a water molecule denoted 491. The hydrophobic side chains 16Trp, 88Met, 135Val are unable to solvate the hydroxyl group. The hydroxyl group of the 90Thr side chain is rotated away, exposing its methyl group to the inhibitor. The water molecule (491) bridges O6 and O4 of the sorbitol. In the structure of the enzyme-cobalt complex determined in the absence of substrate or inhibitor, the active site contains a number of water molecules bound at positions roughly corresponding to the positions of the O1, O2, O3, O4 and O5 of the inhibitor in the enzyme-sorbitol-cobalt complex. However, the environment corresponding to the O6 position is not able to accommodate a water molecule. This provides additional evidence that the hydroxyl group on C6 is not properly solvated.

The substitutions which have been made in the collection of target residues (by applying criteria a–e) were aimed to increase the polarity of the environment of the substrate hydroxyl groups, particularly of the O6, and to increase the flexibility of the active site to accommodate the larger substrate.

Amongst others the following single and combined point mutations have been made, leading to the intended changes in glucose specificity.

25Ala to Lys: introduction of a positively charged residue at a distance of 6 to 8Å of the O1, O2 and O3 of the substrate. Disruption of the water structure in the interface. Displacement of 26Phe, which shapes the hydrophobic pocket accommodating the C1 aliphatic hydrogens of the substrate.

243His to Asn: increased flexibility due to changes in the protein-water hydrogen bonding network in the interior of the barrel.

290His to Asn: increased flexibility due to changes in the protein-water hydrogen bonding network in the interior of the barrel, displacement of water.

290His to Asn combined with 253Lys to Arg: the 253Lys to Arg mutation is introduced to increase stability or prevent glycation (EP-A-0351029) which leads to irreversible inactivation.

88Met to Ser: increasing the polarity of the O6 binding pocket, increasing flexibility by locally altering the packing of the protein.

88Met to Ser combined with 243His to Asn: increasing the polarity of the O6 binding pocket, increasing flexibility by locally altering the packing of the protein.

88Met to Ser combined with 290His to Asn: increasing flexibility due to changes in the protein-water hydrogen bonding network in the interior of the barrel, displacement of water, increasing the polarity of the O6 binding pocket.

90Thr to Ser: altered flexibility of the side chain, increasing flexibility by locally altering the packing of the protein, altering the environment of a substrate bound water molecule (492).

90Thr to Ser combined with 135Val to Gln: altered flexibility of the side chain at position 90, increasing flexibility by locally altering the packing of the protein, altering the environment of a substrate bound water molecule (492), replacement of hydrophobic environment by a polar residue, possibility of a direct hydrogen bond between the glutamine and the C6 hydroxyl group.

90Thr to Ser combined with 135Val to Gln and 215Asn to Ser: altered flexibility, replacement of hydrophobic environment by polar residues, possibility to remove a water molecule, possibility of a direct hydrogen bond between the 90Ser and the C6 hydroxyl group.

135Val to Thr: replacement of hydrophobic environment by a polar residue.

135Val to Gln: replacement of hydrophobic environment by a polar residue, possibility of a direct hydrogen bond between the glutamine and the C6 hydroxyl group.

These mutation proposals are meant to exemplify a rationale which can be applied to create novel glucose isomerases with desired specificities. However, it will be clear to those skilled in the art that desired mutants can be obtained by changing target residues into amino acids differing from the mentioned ones in a similar manner.

Replacing, Removing, Shifting Bound Water Molecules in the Active Site

From comparison of the sorbitol structure with the xylitol structure it appears that particular water molecules may interfere with proper glucose binding. Replacement of this water by an appropriate amino acid side chain, or moving the position of the water by introducing a shorter side chain at the appropriate position may cause an increase in affinity.

Glucose isomerase mutant H290N, which has an enhanced specificity for glucose ($K_m=250$ mM, $V_{max}=41$ μmoles/min/mg) can serve as an example. The removing or shifting of bound water molecules in the active site of mutant H290N is correlated with the observed increase in activity for glucose. Similar effects may be obtained by shifting other bound water molecules. Water molecules which are in a sphere of 4Å around atoms O3, O4, O5 or O6 of the substrate are candidates to be removed or shifted by mutating neighbouring amino acids.

In the following examples recombinant DNA techniques are applied to introduce point mutations in the gene cloned from *Actinoplanes missouriensis*. The protein is overexpressed in *E. coli*, purified and characterized in vitro and in application conditions as described elsewhere (Van Tilburg, 1983, Thesis: "Engineering aspects of biocatalysts in industrial starch conversion", Delftse Universitaire Pers).

EXPERIMENTAL

Cloning and Expression of the D-Glucose Isomerase Gene

D-glucose isomerase (GI) is synonymously used for D-xylose isomerase (D-xylose) ketol-isomerase (EC 5.3.1.5), an enzyme that converts D-xylose into D-xylulose. The D-glucose isomerase from *Actinoplanes missouriensis* produced by engineered E. coli strains is designated as EcoAmi (DSM) GI. To distinguish the *Actinoplanes missouriensis* gene coding for GI from the analogous *E. coli* xylA gene, the former will be designated as GI.

Methods for manipulation of DNA molecules are described in Maniatis et al. (1982, Cold Spring Harbor Laboratory) and Ausubel et al. (1987, Current Protocols in Molecular Biology, John Wiley & Sons Inc.

New York). Cloning and DNA sequence of the glucose isomerase gene from *Actinoplanes missouriensis* DSM 43046 is described elsewhere (EP-A-0351029). The derived amino acid sequence of GI is numbered and compared with other glucose isomerases in FIG. 2. In the following, the numbering of amino acids refers to FIG. 2.

Wildtype and mutant GI enzymes were produced in *E. coli* strain K514 as described in EP-A-0351029. Ep-A-0351029 specifically describes most of the techniques applied in this application and it is therefore incorporated herein by reference.

Assay of the Enzymatic Activity of the Expression Product

The enzymatic activity of glucose isomerase was assayed as described below (1 unit of enzymatic activity produces 1.0 micromole of product -D-xylulose or D-fructose- per minute; therefore, specific activity -spa- is expressed as units per mg of GI enzymes).

GI activity was assayed directly by measuring the increase in absorbance at 278 nm of xylulose produced at 35° C. by isomerisation of xylose by glucose isomerases. This assay was performed in 50 mM triethanolamine buffer, pH 7.5, containing 10 mM $MgSO_4$, in the presence of 0.1M xylose. The final concentration of glucose isomerase in the assay was $\pm 0.01$ mg/ml, this concentration was precisely determined, prior to dilution in the enzymatic assay mixture, by absorption spectroscopy using an extinction coefficient of 1.08 at 278 nm for a solution of enzyme of 1.0 mg/ml.

In the *D-Sorbitol Dehydrogenase Coupled Assay*, enzymatic determination of D-xylulose was performed at 35° C. as previously described (Kersters-Hilderson et al., Enzyme Microb. Technol. 9 (1987) 145) in 50 mM triethanolamine, pH 7.5, 10 mM $MgSO_4$, and 0.1M xylose, in the presence cf $\pm 2 \times 10^{-8}$M D-sorbitol dehydrogenase (L-iditol NAD oxidoreductase, EC 1.1.14), and 0.15 mM NADH. The final concentration of glucose isomerase in this assay was $\pm 2.5 \times 10^{-3}$ mg/ml, this concentration was precisely determined as described above.

With glucose as a substrate GI activity can be assayed by the measurement of D-fructose produced during the isomerization reaction using the cysteine-carbazole method (CCM) which is based on the reaction of ketosugars with carbazole in acids to yield a purple product (Dische and Borenfreund, J. Biol. Chem. 192 (1951) 583). Alternatively, the D-fructose produced during the isomerization reaction can be determined enzymatically using sorbitol dehydrogenase and NADH.

As a measure of specificity the quotient is $V_{max}/K_m$ is sometimes used (Wells et al., ibid). For mutants the $V_{max}/K_m$ values for xylose and for glucose were routinely calculated. Measurements for xylose parameters are carried out at 35° C., whereas glucose parameters are determined at 60° C. These temperatures are chosen for practical reasons. To find out whether conclusions about relative specificity are generally applicable independent of the measurement temperature, some measurements on xylose were performed at 60° C. for both wildtype and mutant enzymes. It was found that conclusions that could be drawn concerning steady-state kinetic parameters at 60° C. were similar to those at 35° C.

EXAMPLES

Example 1: Mutants with Improved Catalytic Properties

The 3-dimensional structure of *Actinoplanes missouriensis* glucose isomerase was studied to select those residues which upon change might yield an improved substrate binding, catalytic activity or substrate specificity. Residues directly or indirectly (via another residue or water molecule) within 4 from 01–06 of the substrate were selected and changed by site-directed mutagenesis with the aid of the pMa, pMc vector system (Stanssens et al., Nucl. Acids Res. 17 (1989) 4441)

In Table 2 below the enzymatic parameters of several of these selected mutants are shown:

In Table 2 xylose is abbreviated "xy" and glucose is abbreviated "gl".

TABLE 2

In Table 2 xylose is abbreviated "xy" and glucose is abbreviated "gl".

| Mutant | ($\mu$mol/min/mg) $V_{max}$ xy | $V_{max}$ gl | $V_{max}$ gl/xy | $K_m$ xy (mM) | $K_m$ gl (mM) | $K_m$ xy/gl $\times 10^{-2}$ | $V_{max}/K_m$ xy | $V_{max}/K_m$ gl |
|---|---|---|---|---|---|---|---|---|
| Wild Type | 24.20 | 34.80 | 1.43 | 4.80 | 290 | 1.7 | 5.04 | 0.12 |
| A25K | 7.66 | 22.61 | 2.95 | 2.73 | 207 | 1.3 | 2.81 | 0.11 |
| M88S | 19.37 | 29.44 | 1.51 | 7.60 | 263 | 2.9 | 2.55 | 0.11 |
| M88SH243N | 13.90 | 24.98 | 1.79 | 11.92 | 387 | 3.1 | 1.17 | 0.06 |
| M88SH290N | 16.07 | 49.77 | 3.09 | 14.82 | 406 | 3.6 | 1.08 | 0.12 |
| T90S | 37.07 | 32.77 | 0.88 | 16.76 | 180 | 9 | 2.21 | 0.18 |
| T90SV135Q | 0.54 | 19.30 | 36 | 182 | 2822 | 6.4 | 0.00 | 0.01 |
| V135Q | 0.67 | 5.57 | 8.3 | 56.00 | 1120 | 5 | 0.01 | 0.00 |
| V135T | 10.90 | 33.11 | 3.04 | 19.95 | 678 | 3 | 0.55 | 0.05 |
| E186D | 8.51 | 37.90 | 4.45 | 7.00 | 736 | 0.9 | 1.22 | 0.05 |
| E186Q | 0.77 | 2.06 | 2.68 | 1.80 | 57 | 3 | 0.43 | 0.04 |
| H243N | 18.90 | 22.00 | 1.16 | 5.80 | 180 | 3.2 | 3.26 | 0.12 |
| K253RH290N | 26.70 | 49.13 | 1.84 | 12.80 | 331 | 3.9 | 2.09 | 0.15 |
| L258K | 24.23 | 44.17 | 1.82 | 4.44 | 327 | 1.4 | 5.46 | 0.14 |
| H290N | 24.00 | 41.80 | 1.74 | 9.70 | 250 | 4 | 2.47 | 0.17 |
| K294Q | 5.70 | 9.70 | 1.70 | 32.00 | 309 | 10 | 0.18 | 0.03 |
| K294R | 13.80 | 27.52 | 4.82 | 4.50 | 308 | 1.5 | 3.07 | 0.09 |
| T90SV135Q, | 0.93 | 39.6 | 42.60 | 360 | 1000 | 36 | 0.0025 | 0.04 |

TABLE 2-continued

In Table 2 xylose is abbreviated "xy" and glucose is abbreviated "gl".

| Mutant | (μmol/min/mg) | | | $K_m$ xy (mM) | $K_m$ gl (mM) | $K_m$ xy/gl ×10⁻² | $V_{max}/K_m$ xy | $V_{max}/K_m$ gl |
|---|---|---|---|---|---|---|---|---|
| | $V_{max}$ xy | $V_{max}$ gl | $V_{max}$ gl/xy | | | | | |
| N215S | | | | | | | | |

Conditions for determining enzymatic parameters were as follows:
$V_{max}$, xylose: 35° C., 10 mM $Mg^{2+}$, pH 7.5;
$V_{max}$, glucose: 60° C., 10 mM $Mg^{2+}$, pH 7.5;
$K_m$, xylose: 35° C., 10 mM $Mg^{2+}$, pH 7.5;
$K_m$, glucose: 60° C., 10 mM $Mg^{2+}$, pH 7.5.

Activities were measured on purified enzyme. The coupled sorbitol dehydrogenase assay was used for xylose, the cysteine-carbazole or discontinuous sorbitol dehydrogenase method was used for glucose.

Example 2: Glucose Isomerases with Improved Affinity for Glucose

Table 3 summarizes measured values from various mutants compared to wildtype enzyme. It can be seen that all of these mutants have a lower $K_m$ for glucose. This means that the binding of the substrate glucose is enhanced. Moreover, for some of the mutants the $K_m$ for xylose has not improved but became worse, as exemplified in Table 2. Thus, mutants M88S, T90S, T90SV135Q, V135Q, H290N, K294Q, H243N have acquired a better $K_m$xylose/$K_m$glucose ratio as compared to the wild-type enzyme.

TABLE 3

| MUTANT | K(gl) | K(gl)/WT |
|---|---|---|
| E186Q | 57.000 | 0.197 |
| H243N | 180.000 | 0.621 |
| T90S | 180.000 | 0.621 |
| A25K | 207.000 | 0.714 |
| H290N | 250.000 | 0.862 |
| M88S | 203.000 | 0.907 |
| Wildtype | 290.000 | 1.000 |

The Km for glucose is expressed in mM.

Example 3: Glucose Isomerases with Enhanced Catalytic Activity on Glucose

Glucose isomerase mutants with enhanced catalytic activity on glucose are E186D, L258K, H290N and combined mutations with H290N. L258K was not selected using the criteria described in the general methods as the leucine at position 258 is about 10Å away from the substrate or inhibitor.

In Table 4, the $V_{max}$ relative to wildtype $V_{max}$ is shown. An increase from 8.9% to 43% is shown. This will give rise to a faster isomerisation of the preferred substrate glucose.

TABLE 4

| MUTANT | V(gl) | V(gl)/WT |
|---|---|---|
| M88SH290N | 49.770 | 1.430 |
| K253RH290N | 49.130 | 1.412 |
| L258K | 44.170 | 1.269 |
| H290N | 41.800 | 1.201 |
| T90SV135QN215S | 39.600 | 1.138 |
| E186D | 37.900 | 1.089 |
| Wildtype | 34.800 | 1.000 |

The $V_{max}$ for glucose is expressed in micromoles/min/mg.

Mutant H290N shows a $V_{max}$ for glucose of 41.80 which is significantly better than the wildtype enzyme. Moreover, the $V_{max}$xylose has not improved. The ratio $V_{max}$glucose/$V_{max}$xylose of H290N has therefore been improved, rendering this mutant more into a "true" glucose isomerase.

Example 4: Structure of H290N Glucose Isomerase

In the crystal structure of the mutant H290N, it is observed that the amide group of the Asn side chain is superimposable on the imidazole group of w.t. molecule (FIG. 3). As a consequence the amide at 290Asn maintains the hydrogen bond to 245Asp. In addition, the Oδ1 atom of 290Asn can hydrogen bond to the hydroxyl of 12Ser.

The hydroxyl group of 52Thr, hydrogen bonded to ne2 of 290His in the w.t. structures, can no longer hydrogen bond to 290Asn. In the mutant the hydroxyl group of 52Thr is rotated ($X^1$ torsion) in such a way that it hydrogen bonds to a water molecule (wildtype $X^1 = 71°$, mutant $X^1 = -172.5°$). This water molecule present in the mutant structure is positioned as the 88Met sδ atom (distance=0.45Å) in the wildtype. The introduction of a water molecule at this position, which forms a hydrogen bond to 52Thr, forces a reorientation of the side chain of 88Met in the mutant structure as compared to wildtype. In addition the 52Thr side chain hydrogen bonds in the mutant to the main chain hydrogen of 53phe (d=2.23Å).

The reorientation of the 88Met side chain in H290N necessitates the movement of 243His. In addition the water molecule (490), bridging 12Ser to 243His in the wildtype structure, disappears because of steric hindrance with the methyl group of 52Thr and the new orientation of 88Met. 243His adopts another X angle (in w.t. $X^1 = -169°$ and in mutant $X^1 = -77°$) abolishing the hydrogen bond with 215Asn. The space left by the imidazole of 243His is filed with a water molecule (615) which hydrogen bonds to the amide of 215Asn (not shown). In addition, this water molecule hydrogen bonds to a novel water molecule (872) which hydrogen bonds to main chain hydrogen atom of 244Ile.

Additional evidence for the change in flexibility of the side chains in the C6 hydroxyl environment is given by the temperature factors for the residues 52Thr, 88Met and 243His, which is twice as high compared to the wildtype structure.

As a result of the complex rearrangements caused by the H290N mutation, three water molecules are solvating the C6 hydroxyl group of the sorbitol.

This exemplifies that replacing, moving or shifting bond water molecules in the active site can result in desired changes in enzyme activity.

Example 5: Glucose Isomerase with an Improved Substrate Binding

In Table 5 several mutants with improved xylose binding are shown. A25K and E186Q have a decreased $K_m$ for both xylose and glucose. E186Q has also a decreased $K_m$ for fructose. Enzymes with high substrate affinity are preferred under conditions of low substrate concentrations.

TABLE 5

| MUTANT | K(xy) | K(gl) | K(xy)/Kgl) | K(xy)/WT | K(gl)/WT |
|---|---|---|---|---|---|
| E186Q | 1.800 | 57.000 | 0.032 | 0.375 | 0.197 |
| A25K | 2.730 | 207.000 | 0.013 | 0.569 | 0.714 |
| L258K | 4.440 | 327.000 | 0.014 | 0.925 | 1.128 |
| K294R | 4.500 | 308.000 | 0.015 | 0.938 | 1.062 |
| Wildtype | 4.800 | 290.000 | 0.017 | 1.000 | 1.000 |

$K_m$ values are expressed in mM. Note that only E186Q and A25K have an improved affinity for both substrates tested.

Example 6: Mutant with an Improved Specificity for Glucose

The relative specificity is defined as the $V_{max}/K_m$ ratio for xylose divided by the $V_{max}/K_m$ ratio for glucose. Therefore, if the number is smaller than for the wild-type the relative specificity for glucose is increased.

In Table 6 mutant glucose isomerases with an increased relative specificity for glucose are shown. Mutants V135Q, T90SV135Q and T90SV135QN215S have a largely reduced activity on xylose. Even though in absolute terms the activity with glucose is reduced, the ratio of $V_{max}/K_m$ of glucose over xylose has been improved considerably. Therefore these mutants have changed their specificity to become a real glucose isomerase virtually without xylose isomerase activity.

The combination of mutations T90S, V135Q and N215S into a triple mutant shows that these mutations are additive with respect to the kinetic parameters (Table 6).

TABLE 6

| MUTANT | V/K(xy) | V/K(gl) | V/K(xy)/(gl) | r.spec./WT |
|---|---|---|---|---|
| T90SV135Q, N215S | 0.003 | 0.040 | 0.065 | 0.002 |
| N215S | 0.058 | 0.018 | 3.193 | 0.076 |
| T90SV135Q | 0.003 | 0.007 | 0.434 | 0.010 |
| V135Q | 0.012 | 0.005 | 2.402 | 0.057 |
| K294Q | 0.178 | 0.031 | 5.674 | 0.135 |
| M88SH290N | 1.084 | 0.123 | 8.846 | 0.211 |
| V135T | 0.547 | 0.049 | 11.209 | 0.267 |
| E186Q | 0.428 | 0.036 | 11.837 | 0.282 |
| T90S | 2.212 | 0.182 | 12.138 | 0.289 |
| K253RH290N | 2.086 | 0.146 | 14.053 | 0.334 |
| H290N | 2.474 | 0.167 | 14.798 | 0.352 |
| M88SH243N | 1.166 | 0.065 | 18.066 | 0.430 |
| M88S | 2.549 | 0.112 | 22.768 | 0.542 |
| E186D | 1.216 | 0.051 | 23.609 | 0.562 |
| A25K | 2.806 | 0.109 | 25.688 | 0.611 |
| H243N | 3.259 | 0.122 | 26.661 | 0.635 |
| K294R | 3.067 | 0.089 | 34.322 | 0.817 |
| L258K | 5.457 | 0.135 | 40.401 | 0.962 |
| Wildtype | 5.042 | 0.120 | 42.014 | 1.000 |

Example 7: Structural Changes Occurring in the M88SH243N Mutant

Substrate specificity can also be changed by amino acid replacements resulting in amino acids that show a greater side-chain flexibility.

In the crystal structure of the mutant M88SH243N it is observed that the 243Asn and 52Thr adopt multiple conformations, reflecting the increase of flexibility in the side chain environment of the C6 hydroxyl environment of the substrate.

It is also observed that the Cα positions of the adjacent beta barrel strands containing residues 88Ser, 52Thr, 135Val and 177Arg are displaced by 0.3 to 0.5Å, making the interior of the barrel slightly larger.

The space created by the 88Met to 88Ser mutation is filled with an additional water molecule. The observed alternate side chain locations and the slight movement of the barrel allow the introduction of another water molecule and the movement of a water molecule in the C6 hydroxyl direction of the substrate.

Example 8: Mutants with Improved Properties in the Presence of $Mn^{2+}$

In addition to $Mg^{2+}$, $Mn^{2+}$ can be used as a bivalent cation during isomerisation. Although $Mn^{2+}$ is not commonly used in commercial isomerisation processes, its use can be envisaged for applications in which metal ions can be removed from the product or in which metal ions are not relevant for the quality of the product.

Mutant E186Q shows an improved catalytic activity towards glucose in the presence of $Mn^{2+}$, see Table 7:

TABLE 7

| | $V_{max}$ (μmoles/min/mg) | Km(mM) | Conditions |
|---|---|---|---|
| E186Q | | | |
| Xylose | 5.4 | 3.15 | 35° C., 1 mM Mn, pH 7.5 |
| Xylose | 14.4 | 7.83 | 35° C., 2 mM Mn, pH 6.4 |
| Glucose | 22.6 | 387 | 60° C., 1 mM Mn, pH 7.5 |
| Mn | 5.63 | 0.01 | 35° C., 100 mM xylose, pH 7.5 |
| Mn | 14.5 | <0.03 | 35° C., 200 mM xylose, pH 6.4 |
| Wildtype | | | |
| Xylose | 8.6 | 13.2 | 35° C., 1 mM Mn, pH 7.5 |
| Glucose | 6.5 | 1537 | 60° C., 1 mM Mn, Ph 7.5 |
| Mn | 10.2 | 0.0048 | 35° C., 100 mM xylose, pH 7.5 |

The methods used were as in Example 1. The improvement in $V_{max}$glucose is 3- to 4-fold as compared to the wild-type enzyme. The improvement in $K_m$glucose is 4-fold. Since 186E is in the vicinity of the UP metal position (see FIG. 1), it can be envisaged that 186Q is in better concert with the larger $Mn^{2+}$ radius than with the $Mg^{2+}$ radius.

Example 9: Application Testing of the Mutant K253RH290N

Mutant H290N shows an increased activity on glucose as can be seen in Table 4. Table 6 shows that the specificity for glucose is also increased in this mutant. This mutant was immobilized as described in EP-A-351029 (Example 7 of that application). Application testing of the wildtype and this mutant glucose isomerase was performed as described in the same application (Example 8). The stability is indicated by the first order decay constant ($K_d$, the lower the decay constant the more stable the enzyme). Table 8 gives the $K_d$ values for the wildtype and mutant glucose isomerases.

TABLE 8

Decay constants for wildtype and mutant glucose isomerase, immobilized on Lewatit

| | $K_d$ ($\times 10^6$ sec$^{-1}$) |
|---|---|
| Wildtype | 2.5 |
| H290N | 3.1 |
| K253R | 0.7 |

TABLE 8-continued

Decay constants for wildtype and mutant glucose isomerase, immobilized on Lewatit

| | $K_d (\times 10^6 \text{ sec}^{-1})$ |
|---|---|
| H290NK253R | 1.6 |

As can be seen in Table 8, H290N is destabilized as compared with the wildtype glucose isomerase. K253R was found to stabilize the wildtype glucose isomerase by a factor larger than three. Combination of H290N with the stability mutation K253R shows that these characteristics are additive. Furthermore, it can be seen in Table 4 that the activity of K253RH290N on glucose is not negatively influenced by the stability mutation, on the contrary the double mutant shows an even higher activity on this substrate than mutant H290N. As far as the specificity is concerned, in Table 6 it can be seen that the K253R mutation does not substantially influence the specificity of the H290N mutant.

Thus it can be concluded that activity mutants can be stabilized by introducing mutations that have been shown to stabilize the wildtype enzyme.

It is to be understood that the above mentioned examples are meant to demonstrate the concept of the invention and that they are not meant to limit the scope. In view of this it is clear that combinations of the above mentioned mutations combined with other mutations leading to altered characteristics e.g. thermostability, shifted pH optimum or metal binding are within the scope of the subject invention.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 394 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Met  Ser  Val  Gln  Ala  Thr  Arg  Glu  Asp  Lys  Phe  Ser  Phe  Gly  Leu  Trp
 1              5                        10                       15

Thr  Val  Gly  Trp  Gln  Ala  Arg  Asp  Ala  Phe  Gly  Asp  Ala  Thr  Arg  Thr
              20                       25                       30

Ala  Leu  Asp  Pro  Val  Glu  Ala  Val  His  Lys  Leu  Ala  Glu  Ile  Gly  Ala
          35                       40                       45

Tyr  Gly  Ile  Thr  Phe  His  Asp  Asp  Leu  Val  Pro  Phe  Gly  Ser  Asp
     50                       55                       60

Ala  Gln  Thr  Arg  Asp  Gly  Ile  Ile  Ala  Gly  Phe  Lys  Lys  Ala  Leu  Asp
 65                       70                       75                       80

Glu  Thr  Gly  Leu  Ile  Val  Pro  Met  Val  Thr  Thr  Asn  Leu  Phe  Thr  His
                    85                       90                       95

Pro  Val  Phe  Lys  Asp  Gly  Gly  Phe  Thr  Ser  Asn  Asp  Arg  Ser  Val  Arg
              100                      105                      110

Arg  Tyr  Ala  Ile  Arg  Lys  Val  Leu  Arg  Gln  Met  Asp  Leu  Gly  Ala  Glu
              115                      120                      125

Leu  Gly  Ala  Lys  Thr  Leu  Val  Leu  Trp  Gly  Gly  Arg  Glu  Gly  Ala  Glu
     130                      135                      140

Tyr  Asp  Ser  Ala  Lys  Asp  Val  Ser  Ala  Ala  Leu  Asp  Arg  Tyr  Arg  Glu
145                      150                      155                      160

Ala  Leu  Asn  Leu  Leu  Ala  Gln  Tyr  Ser  Glu  Asp  Arg  Gly  Tyr  Gly  Leu
                    165                      170                      175

Arg  Phe  Ala  Ile  Glu  Pro  Lys  Pro  Asn  Glu  Pro  Arg  Gly  Asp  Ile  Leu
              180                      185                      190

Leu  Pro  Thr  Ala  Gly  His  Ala  Ile  Ala  Phe  Val  Gln  Glu  Leu  Glu  Arg
          195                      200                      205

Pro  Glu  Leu  Phe  Gly  Ile  Asn  Pro  Glu  Thr  Gly  His  Glu  Gln  Met  Ser
     210                      215                      220

Asn  Leu  Asn  Phe  Thr  Gln  Gly  Ile  Ala  Gln  Ala  Leu  Trp  His  Lys  Lys
225                      230                      235                      240
```

```
Leu Phe His Ile Asp Leu Asn Gly Gln His Gly Pro Lys Phe Asp Gln
                245                 250                 255
Asp Leu Val Phe Gly His Gly Asp Leu Leu Asn Ala Phe Ser Leu Val
                260                 265                 270
Asp Leu Leu Glu Asn Gly Pro Asp Gly Ala Pro Ala Tyr Asp Gly Pro
                275                 280                 285
Arg His Phe Asp Tyr Lys Pro Ser Arg Thr Glu Asp Tyr Asp Gly Val
                290                 295                 300
Trp Glu Ser Ala Lys Ala Asn Ile Arg Met Tyr Leu Leu Leu Lys Glu
305                 310                 315                 320
Arg Ala Lys Ala Phe Arg Ala Asp Pro Glu Val Gln Glu Ala Leu Ala
                325                 330                 335
Ala Ser Lys Val Ala Glu Leu Lys Thr Pro Thr Leu Asn Pro Gly Glu
                340                 345                 350
Gly Tyr Ala Glu Leu Leu Ala Asp Arg Ser Ala Phe Glu Asp Tyr Asp
                355                 360                 365
Ala Asp Ala Val Gly Ala Lys Gly Phe Gly Phe Val Lys Leu Asn Gln
                370                 375                 380
Leu Ala Ile Glu His Leu Leu Gly Ala Arg
385                 390
```

( 2 ) INFORMATION FOR SEQ ID NO:2:

( i ) SEQUENCE CHARACTERISTICS:
( A ) LENGTH: 394 amino acids
( B ) TYPE: amino acid
( C ) STRANDEDNESS: single
( D ) TOPOLOGY: linear ( x i ) SEQUENCE DESCRIPTION: SEQ ID NO:2:

```
Met Ser Leu Gln Ala Thr Pro Asp Asp Lys Phe Ser Phe Gly Leu Trp
1                   5                   10                  15
Thr Val Gly Trp Gln Ala Arg Asp Ala Phe Gly Asp Ala Thr Arg Pro
                20                  25                  30
Val Leu Asp Pro Ile Glu Ala Val His Lys Leu Ala Glu Ile Gly Ala
                35                  40                  45
Tyr Gly Val Thr Phe His Asp Asp Asp Leu Val Pro Phe Gly Ala Asp
                50                  55                  60
Ala Ala Thr Arg Asp Gly Ile Val Ala Gly Phe Ser Lys Ala Leu Asp
65                  70                  75                  80
Glu Thr Gly Leu Ile Val Pro Met Val Thr Thr Asn Leu Phe Thr His
                85                  90                  95
Pro Val Phe Lys Asp Gly Gly Phe Thr Ser Asn Asp Arg Ser Val Arg
                100                 105                 110
Arg Tyr Ala Ile Arg Lys Val Leu Arg Gln Met Asp Leu Gly Ala Glu
                115                 120                 125
Leu Gly Ala Lys Thr Leu Val Leu Trp Gly Gly Arg Glu Gly Ala Glu
                130                 135                 140
Tyr Asp Ser Ala Lys Asp Val Gly Ala Ala Leu Asp Arg Tyr Arg Glu
145                 150                 155                 160
Ala Leu Asn Leu Leu Ala Gln Tyr Ser Glu Asp Gln Gly Tyr Gly Leu
                165                 170                 175
Pro Phe Ala Ile Glu Pro Lys Pro Asn Glu Pro Arg Gly Asp Ile Leu
                180                 185                 190
Leu Pro Thr Ala Gly His Ala Ile Ala Phe Val Gln Glu Leu Glu Arg
                195                 200                 205
Pro Glu Leu Phe Gly Ile Asn Pro Glu Thr Gly His Glu Gln Met Ser
                210                 215                 220
```

```
Asn  Leu  Asn  Phe  Thr  Gln  Gly  Ile  Ala  Gln  Ala  Leu  Trp  His  Lys  Lys
225                      230                 235                      240

Leu  Phe  His  Ile  Asp  Leu  Asn  Gly  Gln  His  Gly  Pro  Lys  Phe  Asp  Gln
               245                      250                           255

Asp  Leu  Val  Phe  Gly  His  Gly  Asp  Leu  Leu  Asn  Ala  Phe  Ser  Leu  Val
               260                      265                      270

Asp  Leu  Leu  Glu  Asn  Gly  Pro  Asp  Gly  Gly  Pro  Ala  Tyr  Asp  Gly  Pro
          275                      280                      285

Arg  His  Phe  Asp  Tyr  Lys  Pro  Ser  Arg  Thr  Glu  Asp  Phe  Asp  Gly  Val
     290                      295                      300

Trp  Glu  Ser  Ala  Lys  Asp  Asn  Ile  Arg  Met  Tyr  Leu  Leu  Leu  Lys  Glu
305                      310                 315                           320

Arg  Ala  Lys  Ala  Phe  Arg  Ala  Asp  Pro  Glu  Val  Gln  Ala  Ala  Leu  Ala
                    325                      330                      335

Glu  Ser  Lys  Val  Asp  Glu  Leu  Arg  Thr  Pro  Thr  Leu  Asn  Pro  Gly  Glu
               340                      345                      350

Thr  Tyr  Ala  Asp  Leu  Leu  Ala  Asp  Arg  Ser  Ala  Phe  Glu  Asp  Tyr  Asp
          355                      360                      365

Ala  Asp  Ala  Val  Gly  Ala  Lys  Gly  Tyr  Gly  Phe  Val  Lys  Leu  Asn  Gln
     370                      375                      380

Leu  Ala  Ile  Asp  His  Leu  Leu  Gly  Ala  Arg
385                      390
```

( 2 ) INFORMATION FOR SEQ ID NO:3:

( i ) SEQUENCE CHARACTERISTICS:
        ( A ) LENGTH: 387 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Met  Asn  Tyr  Gln  Pro  Thr  Pro  Glu  Asp  Arg  Phe  Thr  Phe  Gly  Leu  Trp
1                   5                   10                      15

Thr  Val  Gly  Trp  Gln  Gly  Arg  Asp  Pro  Phe  Gly  Asp  Ala  Thr  Arg  Gln
               20                  25                      30

Ala  Leu  Asp  Pro  Ala  Glu  Ser  Val  Arg  Arg  Leu  Ser  Glu  Leu  Gly  Ala
          35                  40                  45

Tyr  Gly  Val  Thr  Phe  His  Asp  Asp  Leu  Ile  Pro  Phe  Gly  Ser  Ser
     50                       55                  60

Asp  Thr  Glu  Arg  Glu  Ser  His  Ile  Lys  Arg  Phe  Arg  Gln  Ala  Leu  Asp
65                  70                  75                           80

Ala  Thr  Gly  Met  Lys  Val  Pro  Met  Ala  Thr  Thr  Asn  Leu  Phe  Thr  His
               85                  90                      95

Pro  Val  Phe  Lys  Asp  Gly  Ala  Phe  Thr  Ala  Asn  Asp  Arg  Asp  Val  Arg
               100                 105                     110

Arg  Tyr  Ala  Leu  Arg  Lys  Thr  Ile  Arg  Asn  Ile  Asp  Leu  Ala  Val  Glu
               115                 120                     125

Leu  Gly  Ala  Ser  Val  Tyr  Val  Ala  Trp  Gly  Gly  Arg  Glu  Gly  Ala  Glu
     130                 135                     140

Ser  Gly  Ala  Ala  Lys  Asp  Val  Arg  Asp  Ala  Leu  Asp  Arg  Met  Lys  Glu
145                 150                     155                      160

Ala  Phe  Asp  Leu  Leu  Gly  Glu  Tyr  Val  Thr  Glu  Gln  Gly  Tyr  Asp  Leu
               165                     170                      175

Lys  Phe  Ala  Ile  Glu  Pro  Lys  Pro  Asn  Glu  Pro  Arg  Gly  Asp  Ile  Leu
               180                     185                      190

Leu  Pro  Thr  Val  Gly  His  Ala  Leu  Ala  Phe  Ile  Glu  Arg  Leu  Glu  Arg
```

```
                        195                       200                         205

Pro  Glu  Leu  Tyr  Gly  Val  Asn  Pro  Glu  Val  Gly  His  Glu  Gln  Met  Ala
             210                      215                      220

Gly  Leu  Asn  Phe  Pro  His  Gly  Ile  Ala  Gln  Ala  Leu  Trp  Ala  Gly  Lys
        225                      230                      235                       240

Leu  Phe  His  Ile  Asp  Leu  Asn  Gly  Gln  Ser  Gly  Ile  Lys  Tyr  Asp  Gln
                            245                      250                      255

Asp  Leu  Arg  Phe  Gly  Ala  Gly  Asp  Leu  Arg  Ala  Ala  Phe  Trp  Leu  Val
                       260                      265                      270

Asp  Leu  Leu  Glu  Arg  Ala  Gly  Tyr  Ala  Gly  Pro  Arg  His  Phe  Asp  Phe
                  275                      280                      285

Lys  Pro  Pro  Arg  Thr  Glu  Asp  Phe  Asp  Gly  Val  Trp  Ala  Ser  Ala  Ala
             290                      295                      300

Gly  Cys  Met  Arg  Asn  Tyr  Leu  Ile  Leu  Lys  Asp  Arg  Ala  Ala  Ala  Phe
        305                      310                      315                       320

Arg  Ala  Asp  Pro  Gln  Val  Gln  Glu  Ala  Leu  Ala  Ala  Ala  Arg  Leu  Asp
                            325                      330                       335

Glu  Leu  Ala  Arg  Pro  Thr  Ala  Glu  Asp  Gly  Leu  Ala  Ala  Leu  Leu  Ala
                       340                      345                       350

Asp  Arg  Ser  Ala  Tyr  Asp  Thr  Phe  Asp  Val  Asp  Ala  Ala  Ala  Ala  Arg
                  355                      360                      365

Gly  Met  Ala  Phe  Glu  His  Leu  Asp  Gln  Leu  Ala  Met  Asp  His  Leu  Leu
        370                      375                      380

Gly  Ala  Arg
        385
```

( 2 ) INFORMATION FOR SEQ ID NO:4:

( i ) SEQUENCE CHARACTERISTICS:
        ( A ) LENGTH: 388 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
        Met  Ser  Phe  Gln  Pro  Thr  Pro  Glu  Asp  Arg  Phe  Thr  Phe  Gly  Leu  Trp
        1                   5                        10                       15

Thr  Val  Gly  Trp  Gln  Gly  Arg  Asp  Pro  Phe  Gly  Asp  Ala  Thr  Arg  Pro
                       20                       25                       30

Ala  Leu  Asp  Pro  Val  Glu  Thr  Val  Gln  Arg  Leu  Ala  Glu  Leu  Gly  Ala
                  35                       40                       45

Tyr  Gly  Val  Thr  Phe  His  Asp  Asp  Asp  Leu  Ile  Pro  Phe  Gly  Ser  Ser
             50                       55                       60

Asp  Thr  Glu  Arg  Glu  Ser  His  Ile  Lys  Arg  Phe  Arg  Gln  Ala  Leu  Asp
        65                       70                       75                       80

Ala  Thr  Gly  Met  Thr  Val  Pro  Met  Ala  Thr  Thr  Asn  Leu  Phe  Thr  His
                            85                       90                       95

Pro  Val  Phe  Lys  Asp  Gly  Gly  Phe  Thr  Ala  Asn  Asp  Arg  Asp  Val  Arg
                       100                      105                      110

Arg  Tyr  Ala  Leu  Arg  Lys  Thr  Ile  Gly  Asn  Ile  Asp  Leu  Ala  Ala  Glu
                  115                      120                      125

Leu  Gly  Ala  Lys  Thr  Tyr  Val  Ala  Trp  Gly  Gly  Arg  Glu  Gly  Ala  Glu
             130                      135                      140

Ser  Gly  Gly  Ala  Lys  Asp  Val  Arg  Asp  Ala  Leu  Asp  Arg  Met  Lys  Glu
        145                      150                      155                       160

Ala  Phe  Asp  Leu  Leu  Gly  Glu  Tyr  Val  Thr  Ala  Gln  Gly  Tyr  Asp  Leu
                            165                      170                      175
```

```
Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
            195                 200                 205

Pro Glu Leu Tyr Gly Val Asn Pro Glu Val Gly His Glu Gln Met Ala
            210                 215                 220

Gly Leu Asn Phe Pro His Gly Ile Ala Gln Ala Leu Trp Ala Gly Lys
225                         230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Thr Ala Gly Tyr Glu Gly Pro Arg His Phe Asp Phe
            275                 280                 285

Lys Pro Pro Arg Thr Glu Asp Phe Asp Gly Val Trp Ala Ser Ala Ala
            290                 295                 300

Gly Cys Met Arg Asn Tyr Leu Ile Leu Lys Asp Arg Ala Ala Ala Phe
305                         310                 315                 320

Arg Ala Asp Pro Glu Val Gln Glu Ala Leu Arg Ala Ala Arg Leu Asp
            325                 330                 335

Gln Leu Ala Gln Pro Thr Ala Ala Asp Gly Leu Asp Ala Leu Leu Ala
            340                 345                 350

Asp Arg Ala Ala Phe Glu Asp Phe Asp Val Asp Ala Ala Ala Ala Arg
            355                 360                 365

Gly Met Ala Phe Glu His Leu Asp Gln Leu Ala Met Asp His Leu Leu
            370                 375                 380

Gly Ala Arg Gly
385
```

( 2 ) INFORMATION FOR SEQ ID NO:5:

( i ) SEQUENCE CHARACTERISTICS:
        ( A ) LENGTH: 347 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Met Ser Tyr Gln Pro Thr Pro Glu Asp Arg Phe Ser Phe Gly Leu Trp
1               5                   10                  15

Thr Val Gly Trp Gln Gly Arg Asp Pro Phe Gly Asp Ala Thr Arg Arg
            20                  25                  30

Pro Leu Asp Pro Val Gly Thr Val Gln Arg Leu Ala Glu Leu Gly Ala
            35                  40                  45

Tyr Gly Val Thr Phe His Asp Asp Asp Leu Ile Pro Phe Gly Ala Ser
        50                  55                  60

Glu Ala Glu Arg Glu Ala His Val Lys Arg Phe Arg Gln Ala Leu Asp
65                      70                  75                  80

Ala Thr Gly Met Thr Val Pro Met Ala Thr Thr Asn Leu Phe Thr His
                85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
            115                 120                 125

Leu Gly Ala Arg Thr Tyr Val Ala Trp Gly Gly Arg Glu Gly Ala Glu
            130                 135                 140

Ser Gly Ala Ala Lys Asp Val Arg Ala Ala Leu Asp Arg Met Lys Glu
145                 150                 155                 160
```

```
Ala  Phe  Asp  Leu  Leu  Gly  Glu  Tyr  Val  Thr  Ser  Gln  Gly  Tyr  Asp  Ile
               165                170                     175

Arg  Phe  Ala  Ile  Glu  Pro  Lys  Pro  Asn  Glu  Pro  Arg  Gly  Asp  Ile  Leu
               180                185                     190

Leu  Pro  Thr  Val  Gly  His  Ala  Leu  Ala  Phe  Ile  Glu  Arg  Leu  Glu  Arg
               195                200                     205

Pro  Glu  Leu  Phe  Gly  Val  Asn  Pro  Glu  Val  Gly  His  Glu  Gln  Met  Ala
     210                     215                220

Gly  Leu  Asn  Phe  Pro  His  Gly  Ile  Ala  Gln  Ala  Leu  Trp  Ala  Gly  Lys
225                      230                235                           240

Leu  Phe  His  Ile  Asp  Leu  Asn  Gly  Gln  Ser  Gly  Ile  Lys  Tyr  Asp  Gln
               245                250                           255

Asp  Leu  Arg  Phe  Gly  Ala  Gly  Asp  Leu  Arg  Ala  Ala  Phe  Trp  Leu  Val
               260                265                     270

Asp  Leu  Leu  Glu  Ser  Ser  Gly  Tyr  Asp  Gly  Pro  Arg  His  Phe  Asp  Phe
          275                     280                     285

Lys  Pro  Pro  Arg  Thr  Glu  Asp  Leu  Asp  Gly  Val  Trp  Ala  Ser  Ala  Ala
     290                     295                300

Gly  Cys  Met  Arg  Asn  Tyr  Leu  Ile  Leu  Lys  Glu  Arg  Ser  Ala  Ala  Phe
305                      310                315                           320

Arg  Ala  Asp  Pro  Glu  Val  Gln  Glu  Ala  Leu  Arg  Ala  Ser  Arg  Leu  Asp
               325                     330                           335

Gln  Leu  Ala  Gln  Pro  Thr  Ala  Ala  Asp  Gly  Leu
               340                     345
```

(2) INFORMATION FOR SEQ ID NO:6:

(i) SEQUENCE CHARACTERISTICS:
        (A) LENGTH: 395 amino acids
        (B) TYPE: amino acid
        (C) STRANDEDNESS: single
        (D) TOPOLOGY: linear (xi) SEQUENCE DESCRIPTION: SEQ ID NO:6:

```
Met  Ser  Val  Gln  Pro  Thr  Pro  Ala  Asp  His  Phe  Thr  Phe  Gly  Leu  Trp
1               5                    10                          15

Thr  Val  Gly  Trp  Thr  Gly  Ala  Asp  Pro  Phe  Gly  Val  Ala  Thr  Arg  Lys
               20                     25                     30

Asn  Leu  Asp  Pro  Val  Glu  Ala  Val  His  Lys  Leu  Ala  Glu  Leu  Gly  Ala
          35                     40                      45

Tyr  Gly  Ile  Thr  Phe  His  Asp  Asn  Asp  Leu  Ile  Pro  Phe  Asp  Ala  Thr
     50                     55                     60

Glu  Ala  Glu  Arg  Glu  Lys  Ile  Leu  Gly  Asp  Phe  Asn  Gln  Ala  Leu  Lys
65                       70                     75                           80

Asp  Thr  Gly  Leu  Lys  Val  Pro  Met  Val  Thr  Thr  Asn  Leu  Phe  Ser  His
               85                     90                           95

Pro  Val  Phe  Lys  Asp  Gly  Phe  Thr  Ser  Asn  Asp  Arg  Ser  Ile  Arg
               100                    105                    110

Arg  Phe  Ala  Leu  Ala  Lys  Val  Leu  His  Asn  Ile  Asp  Leu  Ala  Ala  Glu
               115                    120                    125

Met  Gly  Ala  Glu  Thr  Phe  Val  Met  Trp  Gly  Gly  Arg  Glu  Gly  Ser  Glu
     130                    135                    140

Tyr  Asp  Gly  Ser  Lys  Asp  Leu  Ala  Ala  Ala  Leu  Asp  Arg  Met  Arg  Glu
145                     150                    155                          160

Gly  Val  Asp  Thr  Ala  Ala  Gly  Tyr  Ile  Lys  Asp  Lys  Gly  Tyr  Asn  Leu
               165                    170                    175

Arg  Ile  Ala  Leu  Glu  Pro  Lys  Pro  Asn  Glu  Pro  Arg  Gly  Asp  Ile  Phe
```

|     |     |     |     | 180 |     |     |     |     | 185 |     |     |     |     | 190 |     |
| --- | --- | --- | --- | --- | --- | --- | --- | --- | --- | --- | --- | --- | --- | --- | --- |
| Leu | Pro | Thr | Val | Gly | His | Gly | Leu | Ala | Phe | Ile | Glu | Gln | Leu | Glu | His |
|     |     | 195 |     |     |     |     | 200 |     |     |     |     | 205 |     |     |     |
| Gly | Asp | Ile | Val | Gly | Leu | Asn | Pro | Glu | Thr | Gly | His | Glu | Gln | Met | Ala |
|     | 210 |     |     |     |     | 215 |     |     |     |     | 220 |     |     |     |     |
| Gly | Leu | Asn | Phe | Thr | His | Gly | Ile | Ala | Gln | Ala | Leu | Trp | Ala | Glu | Lys |
| 225 |     |     |     | 230 |     |     |     |     | 235 |     |     |     |     |     | 240 |
| Leu | Phe | His | Ile | Asp | Leu | Asn | Gly | Gln | Arg | Gly | Ile | Lys | Tyr | Asp | Gln |
|     |     |     |     | 245 |     |     |     |     | 250 |     |     |     |     | 255 |     |
| Asp | Leu | Val | Phe | Gly | His | Gly | Asp | Leu | Thr | Ser | Ala | Phe | Phe | Thr | Val |
|     |     |     | 260 |     |     |     |     | 265 |     |     |     |     |     | 270 |     |
| Asp | Leu | Leu | Glu | Asn | Gly | Phe | Pro | Asn | Gly | Gly | Pro | Lys | Tyr | Thr | Gly |
|     |     | 275 |     |     |     |     | 280 |     |     |     |     | 285 |     |     |     |
| Pro | Arg | His | Phe | Asp | Tyr | Lys | Pro | Ser | Arg | Thr | Asp | Gly | Tyr | Asp | Gly |
|     | 290 |     |     |     | 295 |     |     |     |     | 300 |     |     |     |     |     |
| Val | Trp | Asp | Ser | Ala | Lys | Ala | Asn | Met | Ser | Met | Tyr | Leu | Leu | Leu | Lys |
| 305 |     |     |     | 310 |     |     |     |     | 315 |     |     |     |     |     | 320 |
| Glu | Arg | Ala | Leu | Ala | Phe | Arg | Ala | Asp | Pro | Glu | Val | Gln | Glu | Ala | Met |
|     |     |     |     | 325 |     |     |     |     | 330 |     |     |     |     | 335 |     |
| Lys | Thr | Ser | Gly | Val | Phe | Glu | Leu | Gly | Glu | Thr | Thr | Leu | Asn | Ala | Gly |
|     |     |     | 340 |     |     |     |     | 345 |     |     |     |     | 350 |     |     |
| Glu | Ser | Ala | Ala | Asp | Leu | Met | Asn | Asp | Ser | Ala | Ser | Phe | Ala | Gly | Phe |
|     |     | 355 |     |     |     |     | 360 |     |     |     |     | 365 |     |     |     |
| Asp | Ala | Glu | Ala | Ala | Ala | Glu | Arg | Asn | Phe | Ala | Phe | Ile | Arg | Leu | Asn |
|     | 370 |     |     |     |     | 375 |     |     |     |     | 380 |     |     |     |     |
| Gln | Leu | Ala | Ile | Glu | His | Leu | Leu | Gly | Ser | Arg |     |     |     |     |     |
| 385 |     |     |     |     | 390 |     |     |     |     | 395 |     |     |     |     |     |

( 2 ) INFORMATION FOR SEQ ID NO:7:

( i ) SEQUENCE CHARACTERISTICS:
( A ) LENGTH: 440 amino acids
( B ) TYPE: amino acid
( C ) STRANDEDNESS: single
( D ) TOPOLOGY: linear ( x i ) SEQUENCE DESCRIPTION: SEQ ID NO:7:

| Met | Ala | Gln | Ser | His | Ser | Ser | Val | Asn | Tyr | Phe | Gly | Ser | Val | Asn |
| --- | --- | --- | --- | --- | --- | --- | --- | --- | --- | --- | --- | --- | --- | --- |
| 1 |   |   |   | 5 |   |   |   | 10 |   |   |   |   | 15 |   |
| Lys | Val | Val | Phe | Glu | Gly | Lys | Ala | Ser | Thr | Asn | Pro | Leu | Ala | Phe | Lys |
|   |   |   | 20 |   |   |   |   | 25 |   |   |   |   | 30 |   |   |
| Tyr | Tyr | Asn | Pro | Gln | Glu | Val | Ile | Gly | Gly | Lys | Thr | Met | Lys | Glu | His |
|   |   | 35 |   |   |   |   | 40 |   |   |   |   | 45 |   |   |   |
| Leu | Arg | Phe | Ser | Ile | Ala | Tyr | Trp | His | Thr | Phe | Thr | Ala | Asp | Gly | Thr |
|   | 50 |   |   |   |   | 55 |   |   |   |   | 60 |   |   |   |   |
| Asp | Val | Phe | Gly | Ala | Ala | Thr | Met | Gln | Arg | Pro | Trp | Asp | His | Tyr | Lys |
| 65 |   |   |   | 70 |   |   |   |   | 75 |   |   |   |   |   | 80 |
| Gly | Met | Asp | Leu | Ala | Arg | Ala | Arg | Val | Glu | Ala | Ala | Phe | Glu | Met | Phe |
|   |   |   |   | 85 |   |   |   |   | 90 |   |   |   |   | 95 |   |
| Glu | Lys | Leu | Asp | Ala | Pro | Phe | Phe | Ala | Phe | His | Asp | Arg | Asp | Ile | Ala |
|   |   |   |   | 100 |   |   |   |   | 105 |   |   |   |   | 110 |   |
| Pro | Glu | Gly | Ser | Thr | Leu | Lys | Glu | Thr | Asn | Gln | Asn | Leu | Asp | Ile | Ile |
|   |   |   | 115 |   |   |   |   | 120 |   |   |   |   | 125 |   |   |
| Val | Gly | Met | Ile | Lys | Asp | Tyr | Met | Arg | Asp | Ser | Asn | Val | Lys | Leu | Leu |
|   | 130 |   |   |   |   | 135 |   |   |   |   | 140 |   |   |   |   |
| Trp | Asn | Thr | Ala | Asn | Met | Phe | Thr | Asn | Pro | Arg | Phe | Val | His | Gly | Ala |
| 145 |   |   |   | 150 |   |   |   |   | 155 |   |   |   |   |   | 160 |

```
Ala  Thr  Ser  Cys  Asn  Ala  Asp  Val  Phe  Ala  Tyr  Ala  Ala  Ala  Gln  Val
               165                      170                     175

Lys  Lys  Gly  Leu  Glu  Thr  Ala  Lys  Glu  Leu  Gly  Ala  Glu  Asn  Tyr  Val
               180                      185                     190

Phe  Trp  Gly  Gly  Arg  Glu  Gly  Tyr  Glu  Thr  Leu  Leu  Asn  Thr  Asp  Leu
               195                      200                     205

Lys  Phe  Glu  Leu  Asp  Asn  Leu  Ala  Arg  Phe  Met  His  Met  Ala  Val  Asp
     210                      215                     220

Tyr  Ala  Lys  Glu  Ile  Glu  Tyr  Thr  Gly  Gln  Phe  Leu  Ile  Glu  Pro  Lys
225                      230                     235                     240

Pro  Lys  Glu  Pro  Thr  Thr  His  Gln  Tyr  Asp  Thr  Asp  Ala  Ala  Thr  Thr
               245                      250                     255

Ile  Ala  Phe  Leu  Lys  Gln  Tyr  Gly  Leu  Asp  Asn  His  Phe  Lys  Leu  Asn
               260                      265                     270

Leu  Glu  Ala  Asn  His  Ala  Thr  Leu  Ala  Gly  His  Thr  Phe  Glu  His  Glu
          275                      280                     285

Leu  Arg  Met  Ala  Arg  Val  His  Gly  Leu  Leu  Gly  Ser  Val  Asp  Ala  Asn
     290                      295                     300

Gln  Gly  His  Pro  Leu  Leu  Gly  Trp  Asp  Thr  Asp  Glu  Phe  Pro  Thr  Asp
305                      310                     315                     320

Leu  Tyr  Ser  Thr  Thr  Leu  Ala  Met  Tyr  Glu  Ile  Leu  Gln  Asn  Gly  Gly
               325                      330                     335

Leu  Gly  Ser  Gly  Gly  Leu  Asn  Phe  Asp  Ala  Lys  Val  Arg  Arg  Ser  Ser
               340                      345                     350

Phe  Glu  Pro  Asp  Asp  Leu  Val  Tyr  Ala  His  Ile  Ala  Gly  Met  Asp  Ala
               355                      360                     365

Phe  Ala  Arg  Gly  Leu  Lys  Val  Ala  His  Lys  Leu  Ile  Glu  Asp  Arg  Val
     370                      375                     380

Phe  Glu  Asp  Val  Ile  Gln  His  Arg  Tyr  Arg  Ser  Phe  Thr  Glu  Gly  Ile
385                      390                     395                     400

Gly  Leu  Glu  Ile  Thr  Glu  Gly  Arg  Ala  Asn  Phe  His  Thr  Leu  Glu  Gln
               405                      410                     415

Tyr  Ala  Leu  Asn  Asn  Lys  Thr  Ile  Lys  Asn  Glu  Ser  Gly  Arg  Gln  Glu
               420                      425                     430

Arg  Leu  Lys  Pro  Ile  Leu  Asn  Gln
          435                      440
```

( 2 ) INFORMATION FOR SEQ ID NO:8:

( i ) SEQUENCE CHARACTERISTICS:
( A ) LENGTH: 440 amino acids
( B ) TYPE: amino acid
( C ) STRANDEDNESS: single
( D ) TOPOLOGY: linear ( x i ) SEQUENCE DESCRIPTION: SEQ ID NO:8:

```
Met  Gln  Ala  Tyr  Phe  Asp  Gln  Leu  Asp  Arg  Val  Arg  Tyr  Glu  Gly  Ser
1              5                        10                      15

Lys  Ser  Ser  Asn  Pro  Leu  Ala  Phe  Arg  His  Tyr  Asn  Pro  Asp  Glu  Leu
               20                       25                      30

Val  Leu  Gly  Lys  Arg  Met  Glu  Glu  His  Leu  Arg  Phe  Ala  Ala  Cys  Tyr
               35                       40                      45

Trp  His  Thr  Phe  Cys  Trp  Asn  Gly  Ala  Asp  Met  Phe  Gly  Val  Gly  Ala
     50                       55                      60

Phe  Asn  Arg  Pro  Trp  Gln  Gln  Pro  Gly  Glu  Ala  Leu  Ala  Leu  Ala  Lys
65                       70                      75                      80

Arg  Lys  Ala  Asp  Val  Ala  Phe  Glu  Phe  Phe  His  Lys  Leu  His  Val  Pro
               85                       90                      95
```

```
    Phe  Tyr  Cys  Phe  His  Asp  Val  Asp  Val  Ser  Pro  Glu  Gly  Ala  Ser  Leu
                   100                 105                      110

Lys  Glu  Tyr  Ile  Asn  Asn  Phe  Ala  Gln  Met  Val  Asp  Val  Leu  Ala  Gly
                   115                 120                      125

Lys  Gln  Glu  Glu  Ser  Gly  Val  Lys  Leu  Leu  Trp  Gly  Thr  Ala  Asn  Cys
         130                     135                      140

Phe  Thr  Asn  Pro  Arg  Tyr  Gly  Ala  Gly  Ala  Ala  Thr  Asn  Pro  Asp  Pro
    145                      150                 155                           160

Glu  Val  Phe  Ser  Trp  Ala  Ala  Thr  Gln  Val  Val  Thr  Ala  Met  Glu  Ala
                        165                      170                      175

Thr  His  Lys  Leu  Gly  Gly  Glu  Asn  Tyr  Val  Leu  Trp  Gly  Gly  Arg  Glu
                        180                 185                           190

Gly  Tyr  Glu  Thr  Leu  Leu  Asn  Thr  Asp  Leu  Arg  Gln  Glu  Arg  Glu  Gln
                   195                 200                      205

Leu  Gly  Arg  Phe  Met  Gln  Met  Val  Val  Glu  His  Lys  His  Lys  Ile  Gly
         210                     215                      220

Phe  Gln  Gly  Thr  Leu  Leu  Ile  Glu  Pro  Lys  Pro  Gln  Glu  Pro  Thr  Lys
    225                      230                 235                           240

His  Gln  Tyr  Asp  Tyr  Asp  Ala  Ala  Thr  Val  Tyr  Gly  Phe  Leu  Lys  Gln
                        245                      250                      255

Phe  Gly  Leu  Glu  Lys  Glu  Ile  Lys  Leu  Asn  Ile  Glu  Ala  Asn  His  Ala
                   260                 265                      270

Thr  Leu  Ala  Gly  His  Ser  Phe  His  Glu  Ile  Ala  Thr  Ala  Ile  Ala
         275                     280                      285

Leu  Gly  Leu  Phe  Gly  Ser  Val  Asp  Ala  Asn  Arg  Gly  Asp  Ala  Gln  Leu
         290                     295                      300

Gly  Trp  Asp  Thr  Asp  Gln  Phe  Pro  Asn  Ser  Val  Glu  Glu  Asn  Ala  Leu
    305                      310                 315                           320

Val  Met  Tyr  Glu  Ile  Leu  Lys  Ala  Gly  Gly  Phe  Thr  Thr  Gly  Gly  Leu
                        325                      330                      335

Asn  Phe  Asp  Ala  Lys  Val  Arg  Arg  Gln  Ser  Thr  Asp  Lys  Tyr  Asp  Leu
                   340                 345                      350

Phe  Tyr  Gly  His  Ile  Gly  Ala  Met  Asp  Thr  Met  Ala  Leu  Ala  Leu  Lys
                   355                 360                      365

Ile  Ala  Ala  Arg  Met  Ile  Glu  Asp  Gly  Glu  Leu  Asp  Lys  Arg  Ile  Ala
         370                     375                      380

Gln  Arg  Tyr  Ser  Gly  Trp  Asn  Ser  Glu  Leu  Gly  Gln  Gln  Ile  Leu  Lys
    385                      390                 395                           400

Gly  Gln  Met  Ser  Leu  Ala  Asp  Leu  Ala  Lys  Tyr  Ala  Gln  Glu  His  His
                        405                      410                      415

Leu  Ser  Pro  Val  His  Gln  Ser  Gly  Arg  Gln  Glu  Gln  Leu  Glu  Asn  Leu
                        420                      425                      430

Val  Asn  His  Tyr  Leu  Phe  Asp  Lys
              435                 440
```

( 2 ) INFORMATION FOR SEQ ID NO:9:

( i ) SEQUENCE CHARACTERISTICS:
        ( A ) LENGTH: 439 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Met  Ala  Tyr  Phe  Asn  Asp  Ile  Ala  Pro  Ile  Lys  Tyr  Glu  Gly  Thr  Lys
1                   5                   10                       15

Thr  Lys  Asn  Met  Phe  Ala  Phe  Arg  His  Tyr  Asn  Pro  Glu  Glu  Val  Val
```

|  |  |  | 20 |  |  |  | 25 |  |  |  | 30 |  |  |
|---|---|---|---|---|---|---|---|---|---|---|---|---|---|
| Ala | Gly | Lys<br>35 | Thr | Met | Glu | Glu<br>40 | Gln | Leu | His | Phe<br>45 | Ala | Leu | Ala | Phe | Trp |
| His | Thr<br>50 | Ile | Thr | Met | Asp<br>55 | Gly | Ser | Asp | Pro<br>60 | Phe | Gly | Ala | Thr | Met |
| Glu<br>65 | Arg | Pro | Trp | Asp<br>70 | Leu | Glu | Gly | Ser<br>75 | Glu | Leu | Asp | Arg | Ala | His<br>80 |
| Arg | Arg | Val | Asp<br>85 | Ala | Phe | Phe | Glu | Ile<br>90 | Ala | Glu | Lys | Leu | Gly | Val | Lys<br>95 |
| Tyr | Tyr | Cys<br>100 | Phe | His | Asp | Ile<br>105 | Asp | Ile | Ala | Pro | Thr<br>110 | Gly | Asn | Ser | Leu |
| Lys | Glu | Phe<br>115 | Tyr | Ala | Asn | Leu<br>120 | Asp | Glu | Ile | Thr | Asp<br>125 | His | Leu | Leu | Glu |
| Lys | Gln | Lys<br>130 | Ala | Thr | Gly | Ile<br>135 | Lys | Leu | Leu | Trp | Asn<br>140 | Thr | Ala | Asn | Met |
| Phe<br>145 | Ser | Asn | Pro | Arg | Tyr<br>150 | Met | Asn | Gly | Val | Ser<br>155 | Thr | Ser | Asn | Arg | Ala<br>160 |
| Glu | Val | Phe | Ala | Tyr<br>165 | Gly | Ala | Ala | Gln | Val<br>170 | Lys | Lys | Gly | Leu | Glu<br>175 | Leu |
| Ser | Lys | Lys | Leu<br>180 | Gly | Gly | Glu | Asn | Tyr<br>185 | Val | Phe | Trp | Gly | Gly<br>190 | Arg | Glu |
| Gly | Tyr | Glu<br>195 | Ser | Leu | Leu | Asn | Thr<br>200 | Asp | Met | Gly | Leu | Glu<br>205 | Met | Asp | His |
| Met | Ala<br>210 | Lys | Phe | Phe | His | Leu<br>215 | Ala | Ile | Asp | Tyr | Ala<br>220 | Lys | Ser | Ile | Asn |
| His<br>225 | Leu | Pro | Ile | Phe | Leu<br>230 | Ile | Glu | Pro | Lys | Pro<br>235 | Lys | Glu | Pro | Met | Thr<br>240 |
| His | Gln | Tyr | Asp | Phe<br>245 | Asp | Ser | Ala | Thr | Ala<br>250 | Leu | Ala | Phe | Leu | Gln<br>255 | Lys |
| Tyr | Asp | Leu | Asp<br>260 | Lys | Tyr | Phe | Lys | Leu<br>265 | Asn | Leu | Glu | Thr | Asn<br>270 | His | Ala |
| Trp | Leu | Ala<br>275 | Gly | His | Thr | Phe<br>280 | Glu | His | Glu | Leu | Asn<br>285 | Thr | Ala | Arg | Thr |
| Phe | Asn<br>290 | Ala | Leu | Gly | Ser<br>295 | Ile | Asp | Ala | Asn | Gln<br>300 | Gly | Asn | Tyr | Leu | Leu |
| Gly<br>305 | Trp | Asp | Thr | Asp<br>310 | Glu | Phe | Pro | Thr | Leu<br>315 | Val | Ile | Asp | Ile | Thr | Leu<br>320 |
| Ala | Met | His | Gln | Ile<br>325 | Leu | Leu | Asn | Gly | Gly<br>330 | Leu | Gly | Lys | Gly | Gly<br>335 | Ile |
| Asn | Phe | Asp | Ala<br>340 | Lys | Val | Arg | Arg | Thr<br>345 | Ser | Phe | Lys | Ala | Glu<br>350 | Asp | Leu |
| Ile | Leu | Ala<br>355 | His | Ile | Ala | Gly | Met<br>360 | Asp | Thr | Tyr | Ala | Arg<br>365 | Ala | Leu | Lys |
| Gly | Ala<br>370 | Ala | Ala | Ile | Ile | Glu<br>375 | Asp | Lys | Phe | Leu | Ser<br>380 | Asp | Ile | Val | Asp |
| Glu<br>385 | Arg | Tyr | Ser | Ser | Tyr<br>390 | Arg | Asn | Thr | Glu | Val<br>395 | Gly | Gln | Ser | Ile | Glu<br>400 |
| Asn | Gly | Thr | Ala | Thr<br>405 | Phe | Glu | Ser | Leu | Ala<br>410 | Ala | Phe | Ala | Leu | Glu<br>415 | Tyr |
| Gly | Asp | Asp | Ile<br>420 | Glu | Leu | Asp | Ser | Asn<br>425 | His | Leu | Glu | Tyr | Ile<br>430 | Lys | Ser |
| Val | Leu | Asn | Asp | Tyr | Leu | Val |  |  |  |  |  |  |  |  |  |
|  |  | 435 |  |  |  |  |  |  |  |  |  |  |  |  |  |

We claim:

A glucose isomerase which is a modified form of a naturally occurring glucose isomerase having a determinable three dimensional structure wherein said modification comprises substituting a different amino acid from that occurring at at least one position of said naturally occurring glucose isomerase, wherein said position is identified by:
  selecting all residues and crystallographically assigned water molecules as they exist in said three-dimensional structure which have at least one atom within a sphere of 4 angstroms surrounding the atoms of a substrate bound in the active site of said glucose isomerase and residues which are in van der Waal's contact with said residues and water molecules thus selected, to obtain ia first list of residues and water molecules;
  discarding from said list of residues and water molecules those that are involved in catalysis, cofactor binding and essential intersubunit interactions to obtain a reduced list of residues and water molecules;
  discarding from said reduced list of residues and water molecules those that interfere with the structural roles of those resides discarded from said first list to obtain a twice-reduced list of residues and water molecules,
  wherein said position to be substituted is selected from among those residues on said twice-reduced list.

2. The modified glucose isomerase of claim 1 which has a $V_{max}$ for glucose, measured at temperatures between 20° C. and 85° C., higher than that of the corresponding naturally-occurring glucose isomerase.

3. The modified glucose isomerase of claim 1 which has a $K_m$ for glucose, measured at temperatures between 20° C. and 85° C., lower than that of the corresponding naturally-occurring glucose isomerase.

4. The modified glucose isomerase of claim 1 which has a $V_{max}$ for xylose, measured at temperatures between 20° C. and 85° C., higher than that of the corresponding naturally-occurring glucose isomerase.

5. The modified glucose isomerase of claim 1 which has a $K_m$ for xylose, measured at temperatures between 20° C. and 85° C., lower than that of the corresponding naturally-occurring glucose isomerase.

6. The modified glucose isomerase of claim 1 which has a $V_{max}$ glucose/$V_{max}$ xylose ratio higher than that of the corresponding naturally-occurring glucose isomerase.

7. The modified glucose isomerase of claim 1 which has a $K_m$ xylose/$K_m$ glucose ratio higher than that of the corresponding naturally-occurring glucose isomerase.

8. The modified glucose isomerase of claim 1 wherein the corresponding naturally-occurring glucose isomerase is obtainable from a microorganism of the order Actinomycetales.

9. The modified glucose isomerase of claim 8 wherein said naturally-occurring glucose isomerase is derived from *Actinoplanes missouriensis*.

10. The modified glucose isomerase of claim 1 wherein said replaced amino acid residue is within a sphere of 4 angstroms around the oxygen atoms of a sugar substrate coupled to the active site.

11. The modified glucose isomerase of claim 9 wherein said replaced amino acid is selected from the group consisting of: 15Leu, 17Thr, 20Trp, 25Ala, 27Gly, 52Thr, 53Phe, 55Asp, 57Asp, 87Pro, 88Met, 89Val, 90Thr, 91Thr, 92Asn, 93Leu, 95Thr, 133Thr, 134Leu, 135Val, 136Leu, 138Gly, 140Arg, 179Ala, 180Ile, 182Pro, 186Glu, 215Asn, 216Pro, 218Thr, 219Gly, 243His, 244Ile, 246Leu, 253Lys, 254Phe, 256Gln, 257Asp, 258Leu, 290His, 291Phe, 293Tyr, 294Lys, and 295Pro.

12. The modified glucose isomerase of claim 11 wherein said replacement of at least one amino acid is selected from the group consisting of: A25K, M88S, T90S, V135Q, V135T, E186D, E186Q, N215S, H243N, L258K, H290H, K294Q, and K294R.

13. The modified glucose isomerase of claim 1 which exhibits altered water molecule configuration in a sphere of 4 angstroms around the oxygen atoms of a sugar substrate coupled to the active site.

14. A process for producing the modified glucose isomerase of claim 1 which comprises mutating a DNA sequence encoding a wildtype glucose isomerase at selected nucleotide positions;
  cloning the mutated sequence into an expression vector in such a manner that the DNA sequence can be expressed;
  transforming a host organism or cell with the vector;
  culturing the host organism or cell; and
  isolating the modified glucose isomerase from the culture.

15. A process for producing the modified glucose isomerase of claim 1 which comprises culturing a host organism or cell transformed with a mutated glucose isomerase DNA cloned into an expression vector in such a manner that the DNA sequence can be expressed under conditions which favor expression and
  isolating the modified glucose isomerase from the culture.

16. A method to conduct an enzymatic conversion catalyzed by the glucose isomerase enzyme of claim 1, which method comprises contacting a substrate for said enzyme with said enzyme for a time period and under conditions wherein said conversion occurs.

* * * * *

UNITED STATES PATENT AND TRADEMARK OFFICE
CERTIFICATE OF CORRECTION

PATENT NO. : 5,310,665
DATED : May 10, 1994
INVENTOR(S) : Lambeir et al.

It is certified that error appears in the above-indentified patent and that said Letters Patent is hereby corrected as shown below:

Column 35, line 1, before "A glucose isomerase", please insert --1.--.

Signed and Sealed this

Fifteenth Day of November, 1994

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,310,665
DATED : May 10, 1994
INVENTOR(S) : Lambeir, et. al.

It is certified that error appears in the above-indentified patent and that said Letters Patent is hereby corrected as shown below:

Title page, item [73], Assignee: should read--Plant Genetic Systems, N.V., Brussels, Belgium--.

Signed and Sealed this

Third Day of January, 1995

Attest:

BRUCE LEHMAN

Attesting Officer      Commissioner of Patents and Trademarks